US010925959B2

(12) United States Patent
Qian et al.

(10) Patent No.: US 10,925,959 B2
(45) Date of Patent: Feb. 23, 2021

(54) PORCINE EPIDEMIC DIARRHEA VIRUS S PROTEIN AND SUBUNIT VACCINE THEREOF AS WELL AS METHOD FOR PREPARING SUBUNIT VACCINE AND APPLICATION THEREOF

(71) Applicant: NOVO BIOTECH CORP., Shaoxing (CN)

(72) Inventors: Hong Qian, Shaoxing (CN); Youqiang Wu, Shaoxing (CN); Guanglin Bian, Shaoxing (CN); Qiang Zhang, Shaoxing (CN); Yulan Xu, Shaoxing (CN); Zhijun Bai, Shaoxing (CN); Sufang Wu, Shaoxing (CN); Ying Che, Shaoxing (CN); Yangping Lv, Shaoxing (CN); Yinhe Zha, Shaoxing (CN)

( * ) Notice: Subject to any disclaimer, the term of this patent is extended or adjusted under 35 U.S.C. 154(b) by 0 days.

(21) Appl. No.: 16/600,334

(22) Filed: Oct. 11, 2019

(65) Prior Publication Data

US 2020/0188508 A1 Jun. 18, 2020

Related U.S. Application Data

(63) Continuation of application No. PCT/CN2018/082908, filed on Apr. 13, 2018.

(30) Foreign Application Priority Data

Apr. 13, 2017 (CN) .......................... 201710242260.3
Apr. 3, 2018 (CN) .......................... 201810310540.8

(51) Int. Cl.
| | | |
|---|---|---|
| *A61K 39/00* | (2006.01) | |
| *A61K 39/12* | (2006.01) | |
| *A61K 39/215* | (2006.01) | |
| *C12N 7/00* | (2006.01) | |
| *C07H 21/02* | (2006.01) | |

(52) U.S. Cl.
CPC .............. *A61K 39/215* (2013.01); *C12N 7/00* (2013.01); *A61K 2039/5252* (2013.01); *A61K 2039/552* (2013.01); *C12N 2710/14043* (2013.01); *C12N 2710/14143* (2013.01)

(58) Field of Classification Search
CPC ................... C07K 14/005; C12N 7/00; C12N 2770/20022; C12N 2770/20034; A61K 39/12
See application file for complete search history.

(56) References Cited

U.S. PATENT DOCUMENTS

| | | | |
|---|---|---|---|
| 9,950,061 B2 | 4/2018 | Hernandez et al. | |
| 2015/0283229 A1* | 10/2015 | Hernandez | ............. A61P 37/04 424/186.1 |
| 2018/0064804 A1 | 3/2018 | Zhang et al. | |
| 2018/0207260 A1 | 7/2018 | Hernandez et al. | |

FOREIGN PATENT DOCUMENTS

| | | |
|---|---|---|
| CN | 103992989 A | 8/2014 |
| CN | 105311630 A | 2/2016 |
| CN | 106085969 A | 11/2019 |

OTHER PUBLICATIONS

Internation Search Report of PCT/CN2018/082908, dated Jul. 20, 2018.

* cited by examiner

*Primary Examiner* — Barry A Chestnut
(74) *Attorney, Agent, or Firm* — Erson IP (Nelson IP)

(57) ABSTRACT

The disclosure discloses a porcine epidemic diarrhea virus S protein and a subunit vaccine thereof as well as a method for preparing the subunit vaccine and application thereof. The vaccine contains 30~220 μg of a recombinant porcine epidemic diarrhea virus S protein and a pharmaceutically acceptable ISA 201 VG adjuvant. A method for preparing the subunit vaccine comprises the following steps: (1) cloning the recombinant porcine epidemic diarrhea virus S protein; (2) expressing and purifying the recombinant porcine epidemic diarrhea virus S protein; (3) preparing the recombinant porcine epidemic diarrhea virus S protein prepared in (2) into a water phase; (4) emulsifying the water phase and the ISA 201 VG adjuvant in a volume ratio of 46:54 to obtain a vaccine. The vaccine is high in safety, good in immunogenicity, stable in batches, low in production cost and strong in immunogenicity. On the other hand, CHO cell strains suspending and stably and efficiently expressing the PEDV-S protein are successfully constructed and screened for the first time. The CHO cell strain can express the PEDV-S protein in high yield, the yield can reach 1 g/L, and the expressed PEDV-S protein is easy to purify.

9 Claims, 11 Drawing Sheets

Specification includes a Sequence Listing.

```
OPTI-S    1    GACGTGACCAGGTGCTCTGCCAACACAAATTCAGGCGGTTCTTTAGCAAGTTTAACGTG    60
               |||||| || ||||||| || || ||||| ||||| | ||||| |||| ||||| ||||
PEDV-S    1    GATGTCACTAGGTGCTCAGCTAACACTAATTTTAGGCGTTTCTTTTCAAAATTTAATGTT    60

OPTI-S   61    CAGGCTCCAGCTGTGGTGGTGCTGGGAGGATACCTGCCAATCGGCGAGAATCAGGGCGTG   120
               ||||| ||||||||| || |||| ||||| || || ||| ||| ||||| || |||||
PEDV-S   61    CAGGCGCCTGCAGTTGTTGTACTGGGCGGTTATCTACCTATTGGTGAAAACCAGGGTGTC   120

OPTI-S  121    AACTCTACATGGTATTGTGCTGGACAGCACCCTACCGCTAGCGGAGTGCATGGCATCTTC   180
               || || ||||||| ||||||||| || |||||||| || |||| ||||| ||||| |||
PEDV-S  121    AATTCAACTTGGTACTGTGCTGGCCAACATCCAACTGCTAGTGGCGTTCATGGTATCTTT   180

OPTI-S  181    GTGTCCACATCAGGGGCGGCCATGGCTTCGAGATCGGCATCTCCAGGAGCCCTTTGAC    240
               || ||| ||| | ||| || |||||||| ||||| ||||| |||  || |||||||||
PEDV-S  181    GTTAGCCATATTAGAGGTGGTCATGGCTTTGAGATTGGCATTTCGCAAGAGCCTTTTGAC    240

OPTI-S  241    CCTAGCGGCTACCAGCTGTATCTGCACAAGGCCACCAACGGCAATACCAACGCCACAGCT   300
               ||||| || ||||||||  || |||||||||| | |||||| |||| |||| ||| ||
PEDV-S  241    CCTAGTGGTTACCAGCTTTATTTACATAAGGCTACTAACGGTAACACTAATGCTACTGCG   300

OPTI-S  301    AGACTGCGCATCTGCCAGTTCCCCTCTATCAAGACCCTGGGCCCTACAGCTAACAATGAT   360
               |||||||||||| ||||||||  | | || ||||  || ||||| ||||| || ||||| 
PEDV-S  301    CGACTGCGCATTTGCCAGTTTCCTAGCATTAAAACATTGGGCCCCACTGCTAATAATGAT   360

OPTI-S  361    GTGACCACAGGCCGGAATTGTCTGTTTAACAAGGCCATCCCAGCTCACATGAGCGAGCAT   420
               ||  | ||||| || |||||| | || |||||||||||||||||||| |||||| | ||
PEDV-S  361    GTTACAACAGGTCGTAATTGCCTATTTAACAAAGCCATCCCAGCTCATATGAGTGAACAT   420

OPTI-S  421    TCTGTGGTGGGCATCACCTGGGACAACGATAGAGTGACAGTGTTCTCCGACAAGATCTAC   480
               | ||| ||  | || ||  ||||  | ||  |||| |||| || |  ||||||||| | 
PEDV-S  421    AGTGTTGTCGGAATAACATGGGATAATGATCGTGTCACTGTCTTTTCTGACAAGATCTAT   480

OPTI-S  481    TATTTCTACTTTAAGAACGATTGGAGCCGCGTGGCCACCAAGTGCTATAATTCTGGCGGC   540
               ||||| ||||| ||||| |||||| || | ||| || ||||||| ||||| ||| ||
PEDV-S  481    TATTTTATTTTAAAAATGATTGGTCCCGTGTTGCGACAAAGTGTTACAACAGTGGAGGT   540

OPTI-S  541    TGTGCTATGCAGTACGTGTATGAGCCAACCTACTATATGCTGAATGTGACATCTGCCGGA   600
               |||||  ||||| ||  || |||| ||||| || || ||||  | || | | || || 
PEDV-S  541    TGTGCCATGCAATATGTTACGAACCCACCTATTACATGCTTAATGTTACTAGTGCTGGT   600

OPTI-S  601    GAGGACGGAATCTCCTACCAGCCATGCACAGCCAATTGTATCGGCTATGCCGCTAACGTG   660
               ||||| ||  | |  || || || ||||| ||| || || | ||| ||||| |||| |
PEDV-S  601    GAGGATGGTATTTCTTATCAACCCTGTACAGCTAATTGCATTGGTTATGCTGCCAATGTA   660

OPTI-S  661    TTCGCTACCGAGCCTAATGGCCACATCCCAGAGGGCTTCTCTTTTAACAATTGGTTTCTG   720
               || ||||| |||||||||||||||| || ||| | ||| ||||| || || |||||| 
PEDV-S  661    TTTGCTACTGAGCCCAATGGCCACATACCAGAAGGTTTAGTTTTAATAATTGGTTTCTT   720

OPTI-S  721    CTGTCCAACGATAGCACCCTGGTGCATGGCAAGGTGGTGTCCAATCAGCCTCTGCTGGTG   780
                ||||||| ||| | ||  | ||||||||  | ||||| || || |  || |||| |
PEDV-S  721    TTGTCCAATGATTCCACTTTGGTGCATGGTAAGGTGGTTCCAACCAACCATTGTTGGTC   780

OPTI-S  781    AACTGCCTGCTGGCTATCCCAAAGATCTACGGCCTGGGCCAGTTCTTTTCCTTCAACCAG   840
               || || ||  |||| || ||||| ||||| |  || || ||  |||| ||| ||||
PEDV-S  781    AATTGTCTTTTGGCCATTCCTAAGATTATGGACTAGGCCAATTTTCTCCTTTAATCAA   840

OPTI-S  841    ACAATCGACGGCGTGTGCAATGGAGCTGCTGTGCAGAGGGCTCCAGAGGCTCTGCGGTTT   900
               || || || ||  |||| || ||||||||||||| ||||| ||||| |||||| | |||
PEDV-S  841    ACGATCGATGGTGTTTGTAATGGAGCTGCTGTGCAGCGTGCACCAGAGGCTCTGAGGTTT   900
```

FIG.7A

```
OPTI-S  901  AATATCAACGATACCAGCGTGATCCTGGCCGAGGGCTCTATCGTGCTGCACACCGCTCTG  960
             ||||| | || ||||| ||||| |||  ||  ||| | ||| | |||||||  |||||
PEDV-S  901  AATATTAATGACACCTCTGTCATTCTTGCTGAAGGCTCAATTGTACTTCATACTGCTTTA  960

OPTI-S  961  GGCACAAACTTCTCCTTCGTGTGCTCCAATTCCAGCGACCCCCATCTGGCCACCTTCGCT  1020
             || ||||| ||  | ||  |||| ||||||| |||||||||  || |||||||||||| 
PEDV-S  961  GGAACAAATTTTTCTTTTGTTTGCAGTAATTCCTCAGATCCTCACTTAGCCACCTTCGCC  1020

OPTI-S 1021  ATCCCACTGGGCGCCATCCAGGTGCCCTACTATTGTTTCCTGAAGGTGGATACCTACAAC  1080
             ||||  ||||| ||||||||||| || ||||||||||| | ||| |||||| |||||||
PEDV-S 1021  ATACCTCTGGGTGCTATCCAAGTACCCTATTATTGTTTTCTTAAAGTGGATACTTACAAC  1080

OPTI-S 1081  AGCACAGTGTATAAGTTCTGGCTGTGCTGCCCCTACCGTGAGGGAGATCGTGATCACA   1140
                || ||| ||||| ||  | ||| ||  || ||||||| || ||||| ||||||| |
PEDV-S 1081  TCCACTGTTTATAAATTCTTGGCTGTTTTACCTCCTACCGTCAGGGAAATTGTCATCACC  1140

OPTI-S 1141  AAGTACGGCGACGTGTATGTGAACGGCTTCGGCTACCTGCACCTGGGCCTGCTGGATGCC  1200
             ||||| || || |||||||| || |||  ||||| ||||||||||| ||    ||||| 
PEDV-S 1141  AAGTATGGTGATGTTTATGTCAATGGGTTGGCTATTGCATCTCGGTTTGTTGGACGCT   1200

OPTI-S 1201  GTGACCATCAACTTCACCGTGCATGGCACCGACGATGACGTGTCCGGCTTCTGGACAATC  1260
             ||  | ||| || |||| ||| ||||||||||||||||||| ||| | |||||||| | 
PEDV-S 1201  GTCACAATTAATTTCACTGTTCATGGCACTGACGATGACGTTTCAGGTTTCTGGACCATA  1260

OPTI-S 1261  GCCAGCACCAACTTGTGGACGCTCTGATCGAGGTGCAGGGCACCGCCATCCAGAGAATC  1320
             || |  ||| |  |||| || || ||  |||| ||| ||| ||| | |||||| |||
PEDV-S 1261  GCATCGACTAATTTTGTTGATGCACTTATCGAAGTTCAAGGAACTGCCATTCAGCGTATT  1320

OPTI-S 1321  CTGTACTGCGATGACCCCGTGTCCAGCTGAAGTGTAGCCAGGTGGCTTTCGACCTGGAT  1380
             ||  | ||| |||| | ||||  |||||||||||| |||| || |||||||| ||| |
PEDV-S 1321  CTTTATTGTGATGATCCTGTTAGCCAACTCAAGTGTTCTCAGGTTGCTTTGACCTTGAC  1380

OPTI-S 1381  GACGGCTTTATCCAATCTCTTCCGCAATCTGCTGTCCCACGAGCAGCCTATCAGCTTC  1440
             || || ||| | ||  |||| |  |||  | |||| |||| | || ||| | |||||
PEDV-S 1381  GATGGTTTCTACCCTATTTCTTCTAGAAAACCTTCTGAGTCATGAACAGCCAATTTCTTTT  1440

OPTI-S 1441  GTGACACTGCCATCTTTCAATGATCACTCCTTTGTGAACATCACCGTGTCCGCCTCCTTC  1500
             || || | |||||| | |||||||| | ||| ||| ||  || || ||||| || || |
PEDV-S 1441  GTTACTTTGCCATCATTTAATGATCATTCTTTTGTTAACATTACTGTCTCTGCGTCCTTT  1500

OPTI-S 1501  GGCGGACATTCTGGAGCCAACCTGATCGCTTCCGACACCACAATCAATGGCTTCAGCTCT  1560
             || || ||| |||  || ||||| | || || |||||  ||| ||||||| | ||| ||
PEDV-S 1501  GGTGGTCATAGTGGTGCCAACCTTATTGCATCTGACACTACTATCAATGGGTTTAGTTCT  1560

OPTI-S 1561  TTTTGCGTGGATACAAGACAGTTCACCATCTCCCTGTTTTACAATGTGACAAACAGCTAC  1620
             || ||  || || |||||||| |||| ||  | ||| ||  ||||| |||||||| |||
PEDV-S 1561  TTCTGTGTTGACACTAGACAATTTACCATTTCACTGTTTTATAACGTTACAAACAGTTAT  1620

OPTI-S 1621  GGCTACGTGTCCAAGAGCCAGGACTCTAACTGTCCCTTCACCCTGCAGTCCGTGAATGAT  1680
             ||||  || || ||  ||||| || ||||  ||||||||||| || | || ||||||||
PEDV-S 1621  GGTTATGTGTCTAAATCACAGGACAGTAATTGCCCTTTCACCTTGCAATCTGTTAATGAT  1680

OPTI-S 1681  TATCTGTCTTCTCCAAGTTTGCGTGAGCACCTCTCTGCTGGCCTCCGCTTGTACAATC   1740
             || ||||||| |  || |||  |||  ||||  |  || || ||||| |  | ||||
PEDV-S 1681  TACCTGTCTTTTAGTAAATTTGTGTTCCACCAGCCTTTGGCTAGTGCCTGTACCATA   1740

OPTI-S 1741  GATCTGTTCGGCTACCTGAGTTTGGCTCTGGCCGTGAAGTTTACCTCCCTGTATTTCCAG  1800
             ||| ||||| | ||||||||||||| |  |||||| || |||| || || |||  ||| 
PEDV-S 1741  GATCTTTTTGGTTACCCTGAGTTTGGTAGTGGTGTTAAGTTTACGTCCCTTTACTTTCAA  1800
```

FIG. 7B

```
OPTI-S  1801  TTTACAAAGGGCGAGCTGATCACCGGCACACCAAAGCCCCTGGAGGGCGTGACCGACGTG  1860
              || |||||||| |||| ||| || |||||| | |||| |||||||| ||||| |||||
PEDV-S  1801  TTCACAAAGGGTGAGTTGATTACTGGCACGCCTAAACCACTTGAAGGTGTCACGGACGTT  1860

OPTI-S  1861  AGCTTCATGACACTGGACGTGTGCACCAAGTACACAATCTATGGCTTTAAGGGCGAGGGC  1920
              || || |||||||||||| ||||| ||||||||||| |||||||||||| ||| |||||
PEDV-S  1861  TCTTTTATGACTCTGGATGTTTGTACCAAGTATACTATCTATGGCTTTAAAGGTGAGGGT  1920

OPTI-S  1921  ATCATCACCCTGACAAACTCCAGCTTCCTGGCCGGCTTTTACTATACATCCGACAGCGGC  1980
              ||||| ||||| ||||| || |||||| ||||| |||||||| |||||| || | |
PEDV-S  1921  ATCATTACCCTTACAAATTCTAGCTTTTGGCAGGTTTTTATTACACATCTGATTCTGGA  1980

OPTI-S  1981  CAGCTGCTGGCCTTCAAGAATGTGACCAGCGGCGCCGTGTACTCTGTGACACCCTGTTCT  2040
              ||| || | ||| ||||||||||| | || | ||| ||| ||| ||| || |||||||
PEDV-S  1981  CAGTTGTTAGCCTTTAAGAATGTCACTAGTGGTGCTGTTTATTCTGTTACGCCATGTTCT  2040

OPTI-S  2041  TTTTCCGAGCAGGCCGCTTATGTGGATGACGATATCGTGGGCGTGATCTCTTCCCTGAGC  2100
              |||| | |||||||| | ||||| |||| ||||| ||| ||| || |||   || |
PEDV-S  2041  TTTTCAGAGCAGGCTGCATATGTTGATGATGATATAGTGGGTGTTATTTCTAGTTTGTCT  2100

OPTI-S  2101  AATTCTACATTCAACAGCACCAGAGAGCTGCCCGGCTTCTTTTACCATAGCAATGATGGC  2160
              || || || || |||||| || ||||| || || | ||| |  |||||| ||||||||
PEDV-S  2101  AACTCCACTTTTAACAGTACTAGGGAGTTGCCTGGTTTCTTCTACCATTCTAATGATGGC  2160

OPTI-S  2161  TCTAACTGCACCGAGCCTGTGCTGGTGTACTCCAACATCGGCGTGTGCAAGTCCGGCAGC  2220
              ||||| ||  | ||||||||| |||||| |      ||||| ||||| ||   |||||
PEDV-S  2161  TCTAATTGTACAGAGCCTGTGTTGGTGTATAGTAACATAGGTGTTTGTAAATCTGGCAGT  2220

OPTI-S  2221  ATCGGCTATGTGCCAAGCCAGCCAGGACAGGTGAAGATCGCTCCAACCGTGACAGGCAAT  2280
              || || ||  ||  ||||||||| || |||| ||||| ||| |   ||| |||||||
PEDV-S  2221  ATTGGCTACGTTCCATCCCAGCCTGGCCAAGTCAAGATTGCACCCACGGTTACTGGGAAT  2280

OPTI-S  2281  ATCTCTATCCCTACCAACTTTTCTATGTCCATCCGCACAGAGTACCTGCAGCTGTATAAC  2340
              || |  || || ||||||||| |||| | |||| ||||| | ||| |||| |||||||
PEDV-S  2281  ATTAGTATTCCACCAACTTTAGTATGAGTATTAGGACAGAATATTTACAGCTTTACAAC  2340

OPTI-S  2341  ACACCCGTGATCGTGGACTGCGCTACCTACGTGTGCAACGGCAATTCCAGATGCAAGCAG  2400
              ||  | ||| | |||| || ||  || || ||| | || || ||||| | ||| ||||
PEDV-S  2341  ACGCCTGTTATTGTTGATTGTGCCACATATGTTTGTAATGGTAACTCTCGTTGTAAACAA  2400

OPTI-S  2401  CTGCTGACCCAGTATACAGCCGCTTGTAAGACCATCGAGTCTGCCCTGCAGCTGTCCGCT  2460
              || |  |||||||| || |||| ||||||||||| |||||| | || |||| |  |||
PEDV-S  2401  TTACTCACCCAGTACACTGCAGCATGTAAGACCATAGAGTCAGCATTACAACTCAGCGCT  2460

OPTI-S  2461  AGGCTGGAGAGCGTGGAGGTGAACTCTATGCTGACAATCTCCGAGGAGAGCCTGCAGCTG  2520
              |||||  |  | ||| | || ||||||||||| |  | |   |||| | ||| || |
PEDV-S  2461  AGGCTTGAGTCTGTTGAAGTTAACTCTATGCTTACTATTTCTGAAGAGTCTCTACAGTTA  2520

OPTI-S  2521  GCCACCATCTCCAGCTTCAATGGCGGCGGCTACAACTTTACCAATGTGCTGGGCGTGTCC  2580
              || ||||| || |||| ||||||  || | ||  |  ||||  |||||  ||| |||
PEDV-S  2521  GCTACCATCAGTTCGTTTAATGGTGGTGGATATAATTTTACTAACGTGCTGGGTGTTCT  2580

OPTI-S  2581  GTGTATGACCCTGCTAGCGGCAGAGTGGTGCAGAAGCGCAGCTTCATCGAGGATCTGCTG  2640
              ||||||||  ||||| ||| || | ||| || | || |   ||| |  |||| || ||
PEDV-S  2581  GTGTATGATCCTGCAAGTGGCAGGGTGGTACAAAAAGGTCTTTATTGAAGACCTGCTT  2640

OPTI-S  2641  TTTAACAAGGTGGTGACCAATGGCCTGGGCACAGTGGACGAGGATTACAAGAGGTGCAGC  2700
              ||||| || ||||| || |||||||| || || ||||| ||| |||| || ||| |  |
PEDV-S  2641  TTTAATAAAGTGGTTACTAATGGCCTTGGTACTGTTGATGAAGACTATAAGCGCTGTTCT  2700
```

```
OPTI-S  2701  AACGGCCGGTCTGTGGCTGACCTGGTGTGCGCTCAGTACTATTCTGGCGTGATGGTGCTG  2760
              ||  ||  ||  ||||| | | | ||| ||  |||| | |||||||| || |||  ||
PEDV-S  2701  AATGGTCGCTCTGTGGCAGATCTAGTCTGTGCACAGTATTACTCTGGTGTCATGGTACTA  2760

OPTI-S  2761  CCAGGCGTGGTGGATGCCGAGAAGCTGCACATGTATTCCGCCTCCCTGATCGGAGGAATG  2820
              ||  |  |||| ||  | ||||||| ||||||||| | |||| | ||||| || |||
PEDV-S  2761  CCTGGTGTTGTTGACGCTGAGAAGCTTCACATGTATAGTGCGTCTCTCATCGGTGGTATG  2820

OPTI-S  2821  GTGCTGGGAGGCTTCACAAGCGCCGCTGCCCTGCCCTTTTCTTACGCTGTGCAGGCCAGA  2880
              ||||| ||||| ||||| | |||||| | ||| || ||| |  | |  | ||| | ||
PEDV-S  2821  GTGCTAGGAGGTTTTACTTCTGCAGCAGCATTGCCTTTTAGCTATGCTGTTCAAGCTAGA  2880

OPTI-S  2881  CTGAACTATCTGGCCCTGCAGACCGACGTGCTGCAGAGGAATCAGCAGCTGCTGGCCGAG  2940
              || || |||||| ||||| || || |  || |||| |||| ||||| ||||| | |||
PEDV-S  2881  CTCAATTATCTTGCTCTACAGACGGATGTTCTACAGCGGAACCAGCAATTGCTTGCTGAG  2940

OPTI-S  2941  TCTTTCAACTCCGCTATCGGCAATATCACATCCGCCTTTGAGAGCGTGAAGGAGTCCATC  3000
              ||||| |||||||||||  | |||||| ||||||||||||||| ||| ||||||| |
PEDV-S  2941  TCTTTTAACTCTGCTATTGGTAATATAACTTCAGCCTTTGAGAGTGTTAAAGAGTCTATT  3000

OPTI-S  3001  AGCCAGACCAGCAAGGGCCTGAACACAGTGGCTCACGCCCTGACCAAGGTGCAGGAGGTG  3060
              ||  | ||  |||||| |||||||| |||||| | |  |||| ||||| ||||| ||
PEDV-S  3001  AGTCAAACTTCCAAGGGTTTGAACACTGTGGCTCATGCGCTTACTAAGGTTCAAGAGGTT  3060

OPTI-S  3061  GTGAACTCCCAGGGAGCTGCCCTGACCCAGCTGACAGTGCAGCTGCAGCATAACTTCCAG  3120
              || |||| |||| | ||  | ||||  || |||| | || || || |||| |||||| |
PEDV-S  3061  GTTAACTCGCAGGGTGCAGCTTTGACTCAACTTACCGTACAGCTGCAACACAACTTCCAA  3120

OPTI-S  3121  GCCATCTCTTCCAGCATCGACGATATCTACTCTAGACTGGATATCCTGTCCGCTGACGTG  3180
              |||||  | | ||  |  |||||||| || ||| ||||| ||| |  ||||| |||| |
PEDV-S  3121  GCCATTTCTAGTTCTATTGATGACATTTACTCTCGACTGGACATTCTTTCAGCCGATGTT  3180

OPTI-S  3181  CAGGTGGATAGACTGATCACAGGCCGCCTGTCCGCTCTGAACGCCTTTGTGGCTCAGACC  3240
              |||||  |  ||| ||||| | || || | ||| |  ||||| |||| | ||||| ||
PEDV-S  3181  CAGGTTGACCGTCTCATCACCGGCAGATTATCAGCACTTAATGCTTTTGTTGCTCAAACC  3240

OPTI-S  3241  CTGACAAAGTACACCGAGGTGCAGGCCAGCAGGAAGCTGGCTCAGCAGAAAGTGAATGAG  3300
              || ||  |||| || ||||| |||| ||||||||||| || ||||| |||| |||||||
PEDV-S  3241  CTCACTAAGTATACTGAGGTTCAGGCTAGCAGGAAGCTAGCACAGCAAAAAGGTAATGAG  3300

OPTI-S  3301  TGCGTGAAGTCTCAGTCCCAGCGGTATGGCTTCTGTGGCGGCGACGGCGAGCACATCTTT  3360
              ||||| || || ||| |||| ||||||||  | ||||| || ||||| ||||||| | |
PEDV-S  3301  TGCGTTAAATCCCAATCTCAGCGTTATGGTTTTTGTGGTGGTGATGGCGAGCACATTTTC  3360

OPTI-S  3361  TCCCTGGTGCAGGCTGCTCCACAGGGACTGCTGTTCCTGCATACCGTGCTGGTGCCTGGC  3420
              ||  ||||| ||||  ||||||| || ||||||||  | |||||||| ||||| | | |
PEDV-S  3361  TCTCTGGTACAGGCAGCACCTCAGGGCCTGCTGTTTTTACATACAGTACTTGTACCGGGT  3420

OPTI-S  3421  GACTTTGTGGATGTGATCGCTATCGCCGGCCTGTGCGTGAACGATGAGATCGCCCTGACA  3480
              |||||||| ||||| || || ||||| || ||||||||||||||||| | |||||||
PEDV-S  3421  GACTTTGTAGATGTTATTGCCATCGCTGGCTTATGCGTTAACGATGAAATTGCCTTGACT  3480

OPTI-S  3481  CTGAGGGAGCCTGGACTGGTGCTGTTCACCCACGAGCTGCAGAATCATACCGCTACAGAG  3540
              ||   | || || || |||| ||||| || |||||   |||||||||||||| || ||
PEDV-S  3481  CTACGTGAGCCTGGCTTAGTCTTGTTTACGCATGAACTTCAAAATCATACTGCGACGGAA  3540

OPTI-S  3541  TACTTCGTGTCTTCCAGGCGGATGTTTGAGCCCAGGAAGCCTACCGTGTCCGACTTTGTG  3600
              ||  | ||| |||| ||||| ||||| ||| |||| || || |||||||| ||||| |
PEDV-S  3541  TATTTGTTTCATCGCAGGCGTATGTTTGAACCTAGAAAACCTACCGTTAGTGATTTTGTT  3600
```

FIG.7D

```
OPTI-S  3601 CAGATCGAGAGCTGCGTGGTGACCTACGTGAACCTGACACGGGACCAGCTGCCTGATGTG 3660
             |  |||  ||||| || ||||||| ||  ||||| |||||  |||||||| || ||||
PEDV-S  3601 CAAATTGAGAGTTGTGTGGTCACCTATGTCAATTTGACTAGAGACCAACTACCAGATGTA 3660

OPTI-S  3661 ATCCCAGACTATATCGATGTGAACAAGACACTGGATGAGATCCTGGCCTCTCTGCCAAAT 3720
             ||||||||  ||  ||||||| ||| | ||| ||||||||  ||  ||||||||||| ||
PEDV-S  3661 ATCCCAGATTACATCGATGTTAACAAAACACTTGATGAGATTTTAGCTTCTCTGCCCAAT 3720

OPTI-S  3721 AGGACCGGACCATCCCTGCCACTGGACGTGTTCAACGCCACCTATCTGAATCTGACAGGC 3780
             ||  |  |||||| |  |||   |||  |||| |  ||||| |||||| || |||| |
PEDV-S  3721 AGAACTGGTCCAAGTCTTCCTTTAGATGTTTTTAATGCCACTTATCTCAATCTCACTGGT 3780

OPTI-S  3781 GAGATCGCTGATCTGGAGCAGAGGAGCGAGTCTCTGCGGAACACCACAGAGGAGCTGCAG 3840
             ||  | ||  || | |||||||| |||| ||||||  |  ||||| | |||||||| ||
PEDV-S  3781 GAAATTGCAGATTTAGAGCAGCGTTCAGAGTCTCTCCGTAATACTACAGAGGAGCTCCAA 3840

OPTI-S  3841 TCCCTGATCTACAATATCAACAATACACTGGTGGATCTGGAGTGGCTGAATCGGGTGGAG 3900
             |  ||||||| | ||||||||||| |||| || ||  ||||||||||  |||| |||||
PEDV-S  3841 AGTCTTATATATAATATCAACAACACACTAGTTGACCTTGAGTGGCTCAACCGAGTTGAG 3900

OPTI-S  3901 ACCTATATC 3909
             || ||  ||
PEDV-S  3901 ACATACATC 3909
```

FIG.7E

PORCINE EPIDEMIC DIARRHEA VIRUS S PROTEIN AND SUBUNIT VACCINE THEREOF AS WELL AS METHOD FOR PREPARING SUBUNIT VACCINE AND APPLICATION THEREOF

CROSS-REFERENCE TO RELATED APPLICATIONS

This application is a continuation of International Patent Application NO: 1 PCT/CN2018/082908 with a filing date of Apr. 13 28, 2018, designating the United States, and further claims priority to Chinese Patent Application No. 201810310540.8 with a filing date of Apr. 3, 2018. The content of the aforementioned applications, including any intervening amendments thereto, are incorporated herein by reference.

TECHNICAL FIELD

The disclosure relates to a porcine epidemic diarrhea virus S protein and a subunit vaccine thereof, a method for preparing the subunit vaccine and application thereof, and a CHO cell strain suspending and stably and efficiently expressing the porcine epidemic diarrhea virus S protein and a method for constructing and screening the cell strain, belonging to the technical field of animal vaccines and veterinary biological products.

BACKGROUND OF THE PRESENT INVENTION

Porcine epidemic diarrhea (PED) is an intestinal infectious disease which is caused by porcine epidemic diarrhea viruses (PEDV) and has main symptoms such as emesis, diarrhea and dehydration. This disease is susceptible to pigs at various ages, especially, nursed piglets within 7 days old, with the death rate of up to 50%~90% after infection. In recent years, the morbidity and the death rate of this disease in China are both increasing, which causes huge economic losses for pig raising industry.

PEDV belongs to coronavirus 1 group of coronaviridae, and has a typical coronavirus morphology. The PEDV particle is polymorphism and trends to be spherical, the periphery of the PEDV particle is enveloped with capsules, the capsule is covered with radial fibrils having an average diameter of about 130 nm. The S protein is a 20 mm ball-arm-shaped glycoprotein extending out of the virus particle capsule, having a molecular weight of about 180-220 kDa and consisting of about 1383 amino acids. This protein is rich in cysteine and contains 29 potential N-glycosylation sites, however, the N-glycosylation sites cannot be cleaved by protease after the virus particles are matured, which greatly reduces the cell fusion and infection of this virus and is also one of reasons why PEDV artificial cells are difficultly cultured. According to similarity of PEDV to conserved sequences of other coronavirus S proteins, the PEDV S protein is divided into two structural domains S1 (1-789 aa) and S2 (790-1383 aa) in which S1 is located on the surface of the virus, has main effects of identifying a receptor and binding to a host cell receptor, and mediating the generation of a neutralizing antibody. S2 is mainly in charge of fusion of a virus capsule and a host cell membrane and conduction of virus RNA into a host cell, thereby causing the infection of cells. Furthermore, the PEDV S protein is also an immunogen protein inducing a humoral immune response of a host. Therefore, the PEDV S protein is a candidate protein for developing a genetic engineering subunit vaccine at present.

Currently, vaccines for preventing and controlling porcine epidemic diarrhea are all almost traditional PEDV attenuated vaccines and inactivated vaccines. But, the inactivated vaccine has weak autoimmune protection force, and has incomplete inactivation to cause a risk of detoxification; the attenuated active vaccine has a risk of reversion to virulence of toxic strains. With quick development and continuous deepening research of a molecular biological technique, researchers start to convert development of PEDV vaccines into development of genetic engineering vaccines having potential advantages. This vaccine has the advantage of safety, efficiency, small side effect, high expression quantity, industrial production and the like. In recent years, many researches focus on expression of a PEDV S1 protein and research of vaccines (for example proteins at sites 21-789 in an expression S1 region of an insect rhabdovirus used in the Chinese invention patent with application number 201610348237.8), and tandem expression of core regions of the S protein (for example 3 core regions of *Escherichia coli* expressing the S protein in series used in the Chinese invention patent with application number 201610256701.0). This is mainly because the PEDV S protein is too large (about 1383aa), gene cloning or protein expression and preparation is difficultly implemented in the technical level of molecular biology. However, a truncated or incomplete PEDV protein is only used as an antigen to result in shortages of incomplete epitope, poor overall immunogenicity relative to a full-length protein and the like, and cause inadequate immune protection. In addition, most of the current expression systems are protokaryon or insect rhabdovirus expression systems that generally have no galactosylated modification or have inadequate galactosylated modification, thereby leading to a fact that the immunogenicity of the expressed protein is inferior to that of the protein of virus particle itself and possibly resulting in inadequate protection strength.

The CHO cell was isolated from an ovary of an adult female hamster in 1957 by Dr. Theodore T. Puck from University of Colorado, and is an epithelial adherent cell. This cell is immortalized, can be passed for more than one hundred generations, and is widely used in bioengineering at present. Relative to other expression systems, the CHO cell has the following advantages: (1) it has an accurate post-transcriptional modification function, and the expressed protein is closest to a natural protein in molecular structure, physicochemical properties and biological functions; (2) it can not only grow adherently but also undergo suspension culture, and has high shear and osmotic pressure tolerance; (3) it has efficient amplification and expression capability of recombinant genes, and exogenous protein genes are stably integrated; (4) it has a product extracellular secretion function, and seldom secretes its own endogenous protein, which facilitates the isolation and purification of downstream protein products; (5) it can be cultured at high density in a suspension culture manner or in a serum-free culture medium, and can be produced on large scale since the culture volume can reach more than 1,000 L.

There are many types of CHO cells, such as DG44, DXB11, HO K1 and CHO-S. Since 1980s~1990s, a DHFR (dihydrofolate reductase-deficient) gene amplification and screening system is industrially used at early stage, and its host cell strain is DG44. When the cell culture medium contains methotrexate (MTX), the dihydrofolate reductase is inhibited, and then this gene is amplified by feedback regulation. The genes within the upstream and downstream range of 100-1,000 kb can be amplified accordingly, and therefore the target genes are inserted into this site range so as to be amplified. Now, many monoclonal antibody production systems are still DG44 DHFR systems. A GS (glutamine synthase) amplification system, which takes CHO-K1 as a host cell, is a novel gene amplification and screening system developed in recent years. It has obvious superiority over the DHFR system and is widely recognized and used throughout the world. Its principle is that GS utilizes ammonia in the cell and glutamic acid to synthesize glutamine while providing energy for ATP hydrolysis. Addition of GS inhibitor L-methionine sulfoxide ammonium (MSX) in a glutamine-deficient culture medium can effectively amplify the GS gene and its bound target gene, thus achieving a purpose of improving the expression level of the target gene. This system has the main advantages: (1) the gene-deficient CHO-K1 cell strain does not need to be used as the host cell; (2) the CHO-K1 cell is stronger and easy to culture; (3) glutamine does not need to be added in the culture medium to avoid a problem that the level of ammonia in the culture system is high due to glutamine decomposition, which reduces the difficulty of process control, and effectively improves cell fermentation density and prolongs cell survival time, However, when the inventor of the disclosure first uses CHO cells to express the PEDV-S protein, it was found that the CHO cells basically do not express the PEDV-S protein when the gene of the PEDV-S protein is not optimized. Therefore, the inventor of the disclosure takes a note that when the CHO cells are used to express the PEDV-S protein, the optimization of a gene sequence is an urgent problem to be solved.

SUMMARY OF PRESENT INVENTION

The technical problem to be solved by the disclosure is, first, to provide a porcine epidemic diarrhea virus S protein which can be industrially produced on large scale and a subunit vaccine thereof as well as a method for preparing the subunit vaccine; second, to overcome the problem that the full-length PEDV S protein is difficult to efficiently express in mammalian cells at present; third, to overcome the defects and risks of inactivated vaccines and attenuated vaccines in preventing and controlling porcine epidemic diarrhea.

According to one aspect of the disclosure, the disclosure provides a porcine epidemic diarrhea virus S protein, wherein the porcine epidemic diarrhea virus S protein is a protein consisting of amino acids shown in SEQ ID NO:2, or a derived protein obtained by performing substitution, deletion or addition of one amino acid or several amino acids on an amino acid sequence shown in SEQ ID NO:2 and having porcine epidemic diarrhea virus S protein immunogenicity. Preferably, the porcine epidemic diarrhea virus S protein is a protein which is expressed by CHO cells and contains high glycosylation. The molecular weight of the glycosylated protein accounts for about 33.3% of that of the porcine epidemic diarrhea virus S protein.

In the technical solution of the disclosure, preferably, the molecular weight of the porcine epidemic diarrhea virus S protein in SDS-PAGE is 210 kDa.

In the technical solution of the disclosure, preferably, the molecular weight of the deglycosylated porcine epidemic diarrhea virus S protein in SDS-PAGE is 140 kDa.

According to another aspect of the disclosure, the disclosure provides a porcine epidemic diarrhea virus S protein subunit vaccine, the vaccine comprising 30~200 µg of a porcine epidemic diarrhea virus S protein according to any one of claims 1~3 and a pharmaceutically acceptable ISA 201 VG adjuvant.

In the technical solution of the disclosure, preferably, the pharmaceutically acceptable adjuvant is an oil in water adjuvant (such as ISA 28 VG adjuvant), a water in oil in water adjuvant (such as ISA 206 VG adjuvant), an oil in water adjuvant (such as ISA 660 VG adjuvant), or a water adjuvant (such as alumina gel adjuvant and ISA 251 VG adjuvant), preferably, ISA 201 VG adjuvant.

In the technical solution of the disclosure, the vaccine also comprises an immunopotentiator; preferably, the immunopotentiator is Quil-A; preferably, the concentration of Quil-A is 300~500 µg/vaccine, preferably, the concentration of Quil-A is 400 µg/vaccine.

According to another aspect of the disclosure, the disclosure also provides a method for preparing a porcine epidemic diarrhea virus S protein subunit vaccine, the method comprising the following steps: (1) cloning a gene of a porcine epidemic diarrhea virus S protein; the cloning a gene of a porcine epidemic diarrhea virus S protein comprising the following steps: 1-1) performing codon optimization on the nucleotide sequence of the porcine epidemic diarrhea virus S protein to obtain OPTI-S; and 1-2) cloning the OPTI-S to an eukaryotic expression vector to obtain a recombinant plasmid; (2) expressing and purifying the recombinant porcine epidemic diarrhea virus S protein; the expressing and purifying the recombinant porcine epidemic diarrhea virus S protein comprising the following steps: 2-1) transfecting the recombinant plasmid containing the porcine epidemic diarrhea virus S protein coding gent to a CHO cell strain; 2-2) culturing, screening and acclimating the CHO cell strain in step 2-1) to obtain a highly-expressed cell strain; and 2-3) performing fermentation culture on the cell strain in step 2-2), and purifying to obtain a recombinant porcine epidemic diarrhea virus S protein; (3) preparing the recombinant porcine epidemic diarrhea virus S protein prepared in step (2) into a water phase; and (4) emulsifying the water phase and an ISA 201 VG adjuvant in a volume ratio of 46:54 to obtain a vaccine.

In the technical solution of the disclosure, preferably, the water phase also comprises an immunopotentiator; preferably, the immunopotentiator is Quil-A, and the concentration of Quil-A is 400 µg/vaccine.

In the technical solution of the disclosure, preferably, the nucleotide sequence of the OPTI-S is as shown in SEQ ID NO:1.

In the technical solution of the disclosure, preferably, the eukaryotic expression vector can be pEE 6.4, pEE12.4, Pgl4.13 or pcDNA3.1, preferably, the eukaryotic expression vector is pEE12.4.

In the technical solution of the disclosure, preferably, the CHO cell can be DG44, DXB11, CHO-K1 or CHO-S cell strains. Preferably, the CHO cell is a CHO-K1 cell.

The disclosure also provides an application of a porcine epidemic diarrhea virus S protein in preparation of a porcine epidemic diarrhea virus S protein subunit vaccine and a relevant diagnostic reagent.

The disclosure also provides an application of a porcine epidemic diarrhea virus S protein recombinant subunit vaccine in preparation of a drug for preventing and treating porcine epidemic diarrhea.

In embodiments of the disclosure, the molecular weight of the purified PEDV-S protein is about 210 kDa; after the PEDV-S protein is digested using deglycosylase, it is found that the molecular weight of the deglycosylated PEDV-S protein is only about 140 kDa, which is consistent to the molecular weight, which is about 143 kDa, of the S protein obtained through amino acid sequence analysis of the S protein. This result indicates that there is a large amount of glycosylated modification, which accounts for about 33.3% of the molecular weight of the whole PEDV-S protein, in the PEDV-S protein expressed by using our CHO eukaryotic expression system.

In embodiments of the disclosure, when the purified PEDV-S protein is deglycosylated and then subjected to Western blot detection using PEDV pig high immune serum, it is found that the deglycosylated PDEV-S protein can not bind to the serum or weakly binds to the serum, indicating that glycosylation of the PEDV-S protein is essential for maintaining the immunogenicity of the PDEV-S protein.

On the one hand, the disclosure explicitly proposes the subunit vaccine prepared by using the PEDV-S protein for the first time. This vaccine overcomes the disadvantages of the prior art that the truncated or incomplete PEDV-S protein is only used as the antigen so as to possibly result in incomplete antigen epitope and relatively poor overall immunogenicity in addition to the advantages of high safety, good immunogenicity, stable batches, low production cost and the like; on the other hand, the CHO cell strain suspending and efficiently secreting and expressing the porcine epidemic diarrhea virus S protein is successfully constructed and screened for the first time, this cell strain can express the porcine epidemic diarrhea virus S protein in high yield, with the yield of up to 1 g/L. The expressed porcine epidemic diarrhea virus S protein is easy to purify (the target protein can be purified only from cell supernatant, because the cell supernatant contains a few of hybrid proteins, purification is relatively convenient and fast; if it is needed to break cells when in purification, purification of the target protein is not facilitated due to many hybrid proteins existing in the cells), and therefore it is easy to produce the porcine epidemic diarrhea virus S protein on a large scale to meet the needs of industrialization, and the subunit vaccine prepared by this protein has good immunogenicity and can induce the pigs to only produce good immune response.

DESCRIPTION OF THE DRAWINGS

FIG. 7A shows comparison results of a PEDV-S protein nucleotide sequence before and after optimization, where OPTI-S (having a nucleotide sequence of SEQ ID NO: 1) represents a sequence after optimization, and PEDV-S (having a nucleotide sequence of SEQ ID NO: 3) represents a sequence before optimization.

FIG. 7B is a continuation of FIG. 7A, and shows comparison result of a PEDV-S protein nucleotide sequence before and after optimization.

FIG. 7C is a continuation of FIG. 7B, and shows comparison result of a PEDV-S protein nucleotide sequence before and after optimization.

FIG. 7D is a continuation of FIG. 7C, and shows comparison result of a PEDV-S protein nucleotide sequence before and after optimization.

FIG. 7E is a continuation of FIG. 7D and shows comparison result of a PEDV-S protein nucleotide sequence before and after optimization.

DETAILED DESCRIPTION OF PREFERRED EMBODIMENTS

Figure 1:
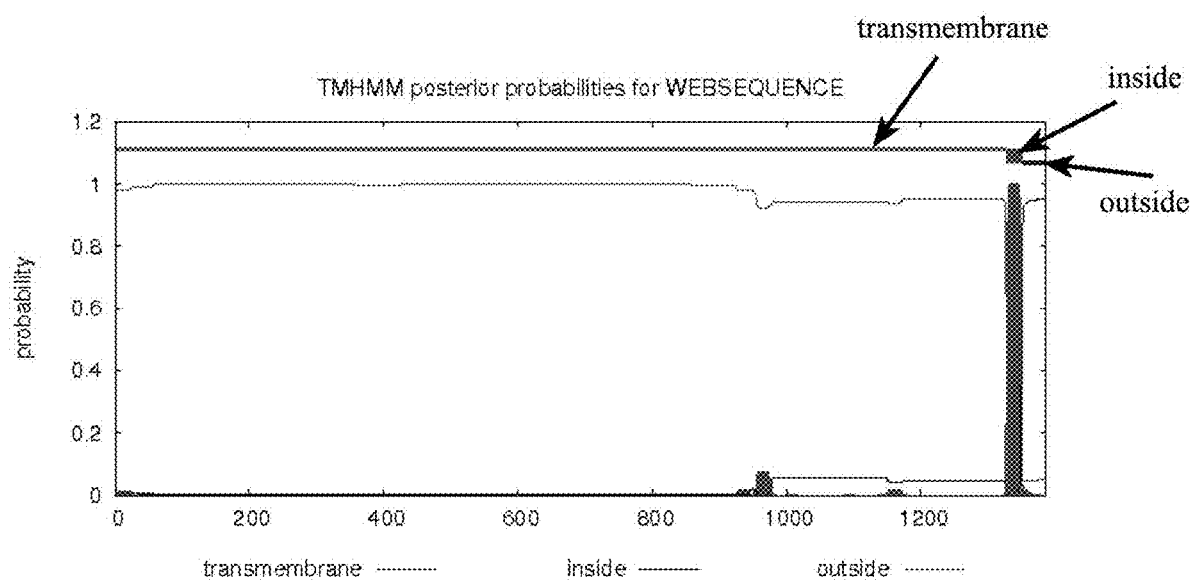
FIG. 1 shows that THMM software predicts a PEDV-S protein transmembrane domain.

The disclosure will be further described in combination with accompany drawings and embodiments. Embodiments of the disclosure are only for illustrating the technical solution of the disclosure, but not limiting the disclosure.

Strains, plasmids and reagents used in embodiments of the disclosure are all commercially available products.

Reagents and medicines used in the disclosure are listed as follows:

CHO-K1 cells are derived from the cell bank of the Institute of life sciences, Chinese Academy of Sciences, and the cell bank of the Institute of life sciences, Chinese Academy of Sciences.

Cell culture mediums and serums are purchased from Gibco Company.

The eukaryotic expression vector pEE12.4 is purchased from the Lin Yuan Biotechnology Co., Ltd.

Ammonium methionine sulfoxide (MSX) is purchased from Sigma Company.

The BCA protein quantitative kit is purchased from Thermo Fisher, USA.

Glycosidase F is purchased from New England Biolabs (UK) Ltd.

HRP-labeled sheep anti-pig IgG II is purchased from EarthOx Life Science.

Quil-A is purchased from Brenntag Biosector.

ISA 201 VG is purchased from France's cyber company.

Example 1: Selection and Codon Optimization of Porcine Epidemic Diarrhea Virus S Protein Gene A PEDV-S protein is a transmembrane protein, which contains an extracellular region, a transmembrane region and an intracellular region. With a typical toxic strain CV777 as reference, the transmembrane region was predicted by TMHMM software (see FIG. 1), a PEDV-S toxic strain that was prevalent in Zhejiang Province in recent years and had been published was used as a template (GenBank: KF840553.1) to design a primer, the sequence of the PEDV-S extracellular region (20D-1320T) was cloned from a pig farm in Zhejiang Province to obtain a PEDV-S nucleotide sequence. The PEDV-S nucleotide sequence was subjected to codon optimization to obtain an OPTI-S sequence as shown in SEQ ID NO: 1, and this work was authorized to Kingsy Biotechnology Co., Ltd.

The sequence (OPTI-S) after optimization was compared with the sequence (PEDV-S) before optimization, it was found that their homology was only 74.1% (see FIG. 7A-7D). We also used the sequence (PEDV-S) before optimization to perform CHO expression, but cannot detect expression of PEDV-S protein, or expression was extremely low and basically cannot be detected. Thus, optimization of the sequence of the PEDV-S protein is an essential step of expression of PEDV-S protein in CHO.

Example 2: Construction of pEE12.4-OPTI-S Recombinant Plasmid 2.1 Amplification of Target Segment OPTI-S Via PCR
2.1.1 PCR Reaction
(1) Design and Synthesis of a Primer

```
Upstream primer:
5'-CGAAGCTTGCCGCCACCATGGACGTGACCAGGTGCTCTG-3'

Downstream primer:
5'-CGGGAATTCTCAATGGTGATGGTGATGGTGGATATAGGTCTC
CAC-3'
```

(2) Loading System 50 µL, as Shown in a Table Below:

| Loading components | Volume (µL) |
|---|---|
| Q5 Mix | 25 |
| Upstream primer (10 µM) | 2.5 |
| Downstream primer (10 µM) | 2.5 |
| OPTI-S | 1 |
| dd H$_2$O | 19 |
| Total volume | 50 |

PCR Amplification Process:

| | | |
|---|---|---|
| 95° C. | 2 min | |
| 95° C. | 30 s | |
| 55° C. | 45 s | 30 cycles |
| 72° C. | 1 min | |
| 72° C. | 10 min | |
| 8° C. | forever | |

2.1.2 Gel Recovery of PCR Products
(1) A sample collection tube, an adsorption column and a collection tube were marked;
(2) the marked hollow EP tube was weighed and its weight was recorded;
(3) a single target DNA strip was carefully cleaved using a scalpel from agarose gel on a gel cleaving instrument and then put into a 1.5 mL clean centrifuge tube;
(4) 600 µL of PC buffer was added to the 1.5 mL of clean centrifuge tube in step (3), and then the tube was placed in 50° C. water bath for about 5 min;

(5) column equilibrium: 500 µL of balance liquid BL was added to an adsorption column CB2 (the adsorption column was put in the collection tube in advance) and then centrifuged for 1 min at 12,000 rpm/min, waste liquid in the collection tube was discarded, and then the adsorption column was put in the collection tube again;

(6) the solution obtained in step (5) was added to the adsorption column CB2 to stand for 2 minutes, the adsorption column was centrifuged for 30 s at 10,000 rpm/min, the waste liquid in the collection tube was discarded, and then the adsorption column CB2 was put into the collection tube;

(7) 600 µL of rinsing solution PW buffer was added into the adsorption column to stand for 3 min, the adsorption column was centrifuged for 30 s at 10,000 rpm/min, the waste liquid in the collection tube was discarded, and the adsorption column CB2 was put into the collection tube;

(8) the step (7) was repeated;

(9) the empty adsorption column was centrifuged for 2 min at 12000 rpm/min, rinsing solution was removed as much as possible, and the adsorption column was placed at room temperature for 10 min to be thoroughly dried in air;

(10) the adsorption column CB2 was put in the collection tube, and 50 µL of Elution buffer (65° C. preheating) was dropwise added in the middle position of an adsorption membrane in a suspending manner to stand for 3 min, and the collection tube was centrifuged for 2 min at 12,000 rpm/min;

(11) the centrifugal tube in step (10) was taken out from a centrifugal machine, the adsorption column CB2 in the middle was discarded, the cap of the centrifugal tube is covered, and the DNA sample in the centrifugal tube is retained;

(12) the DNA samples in step 11 were stored at 4° C., and agarose gel electrophoresis identification gel is prepared to recover the DNA segments.

2.2 PCR Products and Vector Double-Digestion Reaction
(1) a 1.5 mL EP tube required to be used was marked, loading and mixing were carried out in the 1.5 mL EP tube according to a table below: 50 µL reaction system

| Loading component names | Volume (µL) |
|---|---|
| dd H$_2$O | Supplement to 50 |
| 10 × buffer | 5 |
| DNA sample | Volume in 2 µg |
| Hind III | 2.5 |
| EcoR I | 2.5 |

(2) the 1.5 mL EP tube in step (1) was placed in a thermostat water bath pot with a corresponding enzyme optimum temperature to carry out water bath for 2-3 h;
(3) recovery of double-digestion product gel: the above double-digestion system was taken out to undergo agarose gel electrophoresis to recover the DNA segment therein. The method is the same as the method for recovery of PCR product gel in 1.2.1.

2.3 Ligation Reaction
(1) Several 1.5 mL EP tubes were prepared to be placed on an EP tube shelve for standby;
(2) loading and uniform mixing were carried out in the 1.5 mL EP tubes according to a table below;

| Loading component names | Experiment group (μL) | Blank group (μL) |
| --- | --- | --- |
| dd H$_2$O | / | 6 |
| 10 × T4 ligation buffer | 1 | 1 |
| Target segment | 6 | — |
| Vector | 2 | 2 |
| T4 ligase | 1 | 1 |

(3) after loading was completed according to the table in step (2), each of 10 μl reaction system was placed in 16° C. low-temperature cooling liquid circulator to undergo water bath for 10-16 h;

(4) the EP tubes in step (3) were taken out and placed in 65° C. water bath pot to undergo water bath for 15 min;

(5) the EP tubes in step (4) were taken out and stored at 4° C.

1.2.4 Transformation Reaction (1) 10 μL of ligation reaction solution was quickly added to 100 μL of competent cells and uniformly mixed by blowing, and the mixture was subjected to ice bath for 30 min;

(2) the sample tube was taken out and placed in 42° C. water bath for 100 s, and then immediately subjected to ice bath for 2 min;

(3) the sample tube was taken out, add 600 μL of liquid LB culture medium was added in the sample tube on a super-clean workbench, and then the sample tube was placed in a 37° C. constant temperature shaker to be cultured for 1 h at 220 rpm/min;

(4) paving: the sample tube in step (3) was taken out and centrifuged for 2 min at 8,000 rpm/min under room temperature, 600 μL of supernatant was removed, then bacteria at the bottom of the tube were re-suspended with the remained supernatant, the re-suspended bacteria solution was put in the center of a corresponding transformation plate, and the bacteria solution in the center of the transformation plate was evenly paved with a coating rod;

(5) the plate in transformation step (4) was placed in a biochemical incubator to be cultured for 1 h at 37° C., and then the transformation plate was inverted and cultured for 15 h;

(6) the transformation results were observed.

2.5 Plasmid Extraction and Double-Digestion Identification 2.5.1 Plasmid Extraction (1) Monoclonal antibodies were picked with a 10 μL pipette gun head from the transformation plate to 5 mL of ampicillin-resistant LB liquid culture medium to be shaken under 37 C at 220 rpm/min for overnight;

(2) the bacterial liquid was transferred to the 1.5 mL EP tube and centrifuged for 2 min at 12,000 rpm/min under room temperature, and the supernatant was discarded;

(3) 250 μL of plasmid extraction reagent P1 buffer was added to the EP tube in step (2) to completely suspend the bacteria;

(4) 250 μL of P2 buffer was added to the solution in step (3), the centrifugal tube was immediately and gently inverted for 5-10 times to be uniformly mixed, and the centrifugal tube stood for 2-4 min at room temperature;

(5) 350 μL of P3 buffer was added to the solution in step (4), and the centrifugal tube was immediately and gently inverted for 5-10 times to be uniformly mixed, and the centrifugal tube stood for 2-4 min at room temperature;

(6) the solution in step (5) was centrifuged for 10 min at 14,000 rpm/min under room temperature;

(7) the supernatant solution in step (6) was transferred to the center of the adsorption column, the adsorption column was centrifuged for 30 s at 12,000 rpm/min under the room temperature, and the liquid in the collection tube was discarded;

(8) 500 μL of Buffer DW1 was added to the center of the adsorption column, the adsorption column was centrifuged for 30 s at 12,000 rpm/min under room temperature, and the liquid in the collection tube was discarded;

(9) 500 μL of wash solution was added to the center of the adsorption column, the adsorption column was centrifuged for 30 s at 12,000 rpm/min under room temperature, and the liquid in the collection tube was discarded and then this step was repeated again;

(10) the empty adsorption column was centrifuged for 2 min at 12,000 rpm under room temperature;

(11) the adsorption column was placed in a 1.5 μL clean centrifugal tube, and 30 μL of Elution buffer was added to the center of the adsorption membrane, the centrifugal tube stood for 5 min at room temperature and then centrifuged for 2 min at 12,000 rpm under room temperature, and the DNA solution in the tube was preserved.

2.5.2 Double-Digestion Identification (1) a 1.5 mL EP tube required to be used was marked, loading was performed according to a table below: 20 μL reaction system;

| Loading component names | Volume (μL) |
| --- | --- |
| dd H$_2$O | Supplement to 20 μL |
| 10 × buffer | 2 |
| DNA sample | Volume when mass is 1 μg |
| HindIII | 1 |
| EcoR I | 1 |

Figure 2:
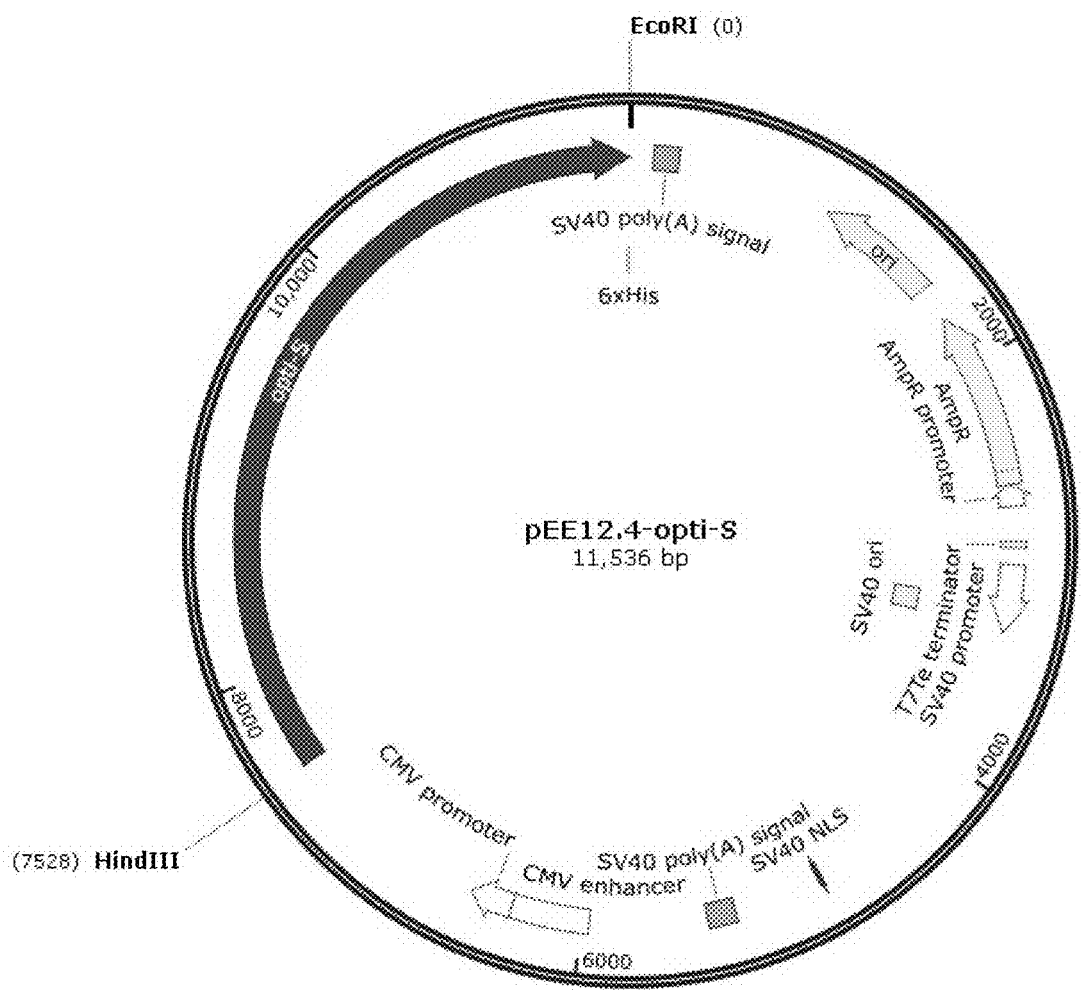
FIG. 2 shows a pEE12.4-OPTI plasmid profile.
Figure 3:
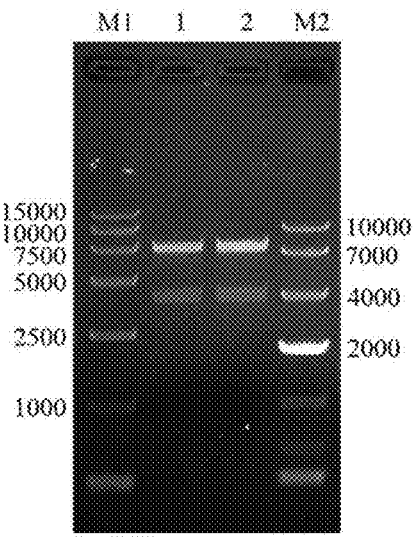
FIG. 3 shows a pEE12.4-OPTI-S double-digestion identification result. 1 and 2 represent PEDV-opti-S plasmid utilizes EcoRI/HindIII double digestion, the size of a vector is about 7,528 kb, the size of a target segment is about 3,930 bp, and the digestion is correct; M1:DL5,000 marker, and M2:DL10,000 marker.

(2) the 20 μL EP tube reaction system in step (1) was placed in a 37° C. constant temperature water bath pot to undergo water bath for 2 h;

(3) the double-digestion system sample in step (2) was subjected to agarose gel electrophoresis to check whether the size of the inserted segment is correct. The experimental results are shown in FIG. 3, 1 and 2 indicate that the PEDV-opti-S plasmid utilizes EcoRI/HindIII double digestion, the size of the vector is about 7,528 bp, the size of the target segment is about 3,930 bp, and the digestion is correct; M1:DL15,000 maker, M2:DL10,000 maker.

(4) the clones where the inserted segment was correct were selected to be sequenced in a sequencing company.

2.6 Maxi Extraction of Endotoxin-Free Plasmids 2.6.1 Extraction of Endotoxin-Free Plasmid (1) Clones which were correctly sequenced were inoculated into 100 mL ampicillin-resistant culture medium to be cultured in a 37° C. constant temperature shaker for 15 h at 220 rpm/min;

(2) the cultured bacteria liquid in step (1) was transferred to a 50 mL centrifugal tube to be centrifuged for 5 min at 8,000 rpm/min under room temperature, the bacteria were collected and the supernatant medium was discarded;

(3) 8 mL of solution P1 was added to the centrifugal tube in step (2) and the bacteria was fully re-suspended with a pipette;

(4) 8 mL of solution P2 was added to the centrifugal tube in step (3), the centrifugal tube was immediately and gently inverted for 6-8 times, and stood for 5 min at room temperature;

(5) 8 mL of solution P4 was added to the centrifugal tube in step (4) and the centrifuge tube was immediately inversed up and down for 6-8 times to be sufficiently and uniformly mixed until white flocculent precipitates occur in the solution, the centrifugal tube was placed for about 10 min at room temperature and centrifuged for 5-10 min at 8,000 rpm/min under room temperature, so that the white precipitates are separated at the bottom of the tube;

(6) the supernatant in step (5) was completely and carefully transferred into a filter CS1, the handle of the filter was slowly pushed, and the filtrate was collected in the 50 mL clean centrifugal tube;

(7) column equilibrium: 2.5 mL of balance liquid BL was added to the adsorption column CP6 (the adsorption column was put into 50 mL collection tube), the adsorption column was centrifuged for 2 min at 8,000 rpm/min under room temperature, the waste liquid in the collection tube was discarded, and the adsorption column was re-placed in the collection tube;

(8) isopropanol whose volume is 0.3 time that of filtrate was added to the filtrate in step (6), the isopropanol and the filtrate were inversed up and down and uniformly mixed and then transferred to the adsorption column CP6, the adsorption column was centrifuged for 2 min at 8,000 rpm/min under room temperature, the liquid in the collection tube was discarded, and the adsorption column CP6 was put into the same collection tube again;

(9) 10 mL of rinsing solution PW was added to the adsorption column CP6 in step (8), the adsorption column was centrifuged for 2 min at 8,000 rpm/min under room temperature, the waste liquid in the collection tube was discarded, and the adsorption column was placed into the collection tube again;

(10) operation step (9) was repeated once;

(11) 3 mL of absolute ethanol was added to the adsorption column CP6 in step (10), the adsorption column was centrifuged for 2 min at 8,000 rpm/min under room temperature, and the waste liquid was discarded;

(12) the adsorption column CP6 in step (11) was placed in the collection tube again, the collection tube was centrifuged for 5 minutes at 8,000 rpm/min under room temperature, the adsorption column CP6 was uncovered and placed at room temperature for several minutes to be dried in air;

(13) the adsorption column in step (12) was put into the 50 mL clean centrifugal tube, 1-2 mL of buffer TB was added into the center of the adsorption membrane, the centrifugal tube stood for 5 min at room temperature and then centrifuged for 2 min at 8,000 rpm/min under room temperature, the eluent in the 50 mL centrifugal tube was completely transferred into the 1.5 mL clean centrifugal tube, the concentration was measured, and the centrifugal tube was stored at −20 C;

(14) 1-2 ml of the obtained plasmid DNA solution was taken and subjected to agarose gel electrophoresis, and electrophoretic result data were preserved.

Example 3: Transfection of CHO-K1 Cells with pEE12.4-OPTI-S Recombinant Plasmids and Establishment of Monoclonal Screening 3.1 CHO-K1 Cell Transfection (1) Preparation: ultraviolet sterilization for 30 minutes in a bio-safety cabinet; DMEM/F, 12 (containing 10% of serum and 1% of double antibody), DMEM/F 12 and PBS were preheated to 37° C. in a 37° C. water bath pot.

(2) Cells (10 cm cell culture dish) were taken out from a 37° C. incubator, the supernatant culture medium was discarded, the cells were washed once with 8 mL of PBS, and PBS was discarded.

(3) 1-2 mL of 0.25% trypsin-EDTA was added to each 10 cm cell culture dish and digested at room temperature for about 2 min. Cells were observed to be shrunk and become round under a microscope, showing a single cell.

(4) 4 mL of DMEM/F12 (containing 10% of serum and 1% of double antibody) was added to end the digestive reaction, and the cells were dispersed by pipette.

(5) The digested cells were transferred to a 15 mL centrifugal tube and the centrifugal tube was centrifuged for 5 min at 200 g under room temperature.

(6) Cells were re-suspended with DMEM/F12 (containing 10% of serum and 1% of double antibody) and counted.

(7) The cells were diluted to $2 \times 10^5$ cells/mL, 2 mL of uniformly mixed cells were taken and added to a six-well plate. The six-well plate was placed in a 37° C. 5% CO2 cell incubator to be incubated for overnight.

(8) The cell culture dish in step (7) was taken out to observe the cell state. When the cell confluence degree reaches 80%-90%, transfection is started. Before transfection, the culture medium is changed into antibiotic-free serum-free DMEMIF12, 2 mL/well.

(9) Dilution of plasmids: the plasmids were diluted with OPTI-MEM, and 2.5 μg of plasmids were added into 125 μL of OPTI-MEM, then 2.5 μL plus was added, and then the above substances were blended, and the mixture stood for 5 min at room temperature.

(10) Dilution with Lipofectamine LTX: 9 μL of Lipofectamine LTX was added in 125 μL of OPTI-MEM, then 2.5 μL plus was added, the above substances were gently and uniformly mixed, and the mixture stood for 5 min at room temperature.

(11) the mixtures in step (10) and step (11) are gently and uniformly mixed, and then the obtained mixture was placed at room temperature for 5 minutes and dropwise added to in a six-well plate to be evenly paved.

(12) The six-well plate was placed in a 37° C., 5% $CO_2$ cell incubator to be incubated for 4-6 h.

(13) Solution change: the supernatant medium was discarded, 2 mL of DMEM/F12 (containing 10% of serum 1% of double antibody) was added, and the six-well plate was placed in 37° C., 5% $CO_2$ cell incubator to be incubated.

3.2 Pressurized Screening

Pressurization was started 24 hours after transfection: cells on the six-well plate were taken out from the 37° C. incubator, the supernatant medium was discarded, and 2 mL of DMEM/F12 (containing 10% of serum+25 μM MSX) was added. Pressurization lasted for 7d. Cells were observed during the pressurization, and solution is changed if there were too many dead cells.

3.3 Monoclonal Screening (1) Monoclonal screening began about 7 days when negative control cells were basically dead by pressurized screening.

(2) The six-well plate was taken out, the culture medium was discarded, the remained substances were washed once with PBS, then 300 μL of 0.25% trypsin-EDTA was added, the above substances were digested at room temperature for about 2 min, 2 mL of DMEM/F12 (containing 10% of serum+25 μM of MSX) was added to end the digestive reaction, and the cells were blown away with a pipette.

(3) The digested cells were transferred to a 15 mL centrifugal tube and the centrifugal tube was centrifuged for 5 min at 200 g under room temperature.

(4) Cells were re-suspended with DMEM/F12 (containing 10% of serum+25 μM MSX) and counted.

(5) Paving: cells were diluted to 5 cells/mL, 200 μL of uniformly mixed cells were taken and added into a 96-well plate, the 96-well plate was placed at 37° C., 5% $CO_2$ cell incubator to be incubated for 4-6 h.

(6) The holes of a single cell were recorded.

(7) When the holes of the single cell in the 96-well plate grow up, the culture medium was discarded, the remained substance was washed once with PBS, 100 μL of 0.25% trypsin-EDTA was added, the mixture was digested at room temperature for about 2 min, 2 mL of DMEM/F12 (containing 10% of serum+25 μM of MSX) was added to end the digestive reaction, and the cells were blown away with a pipette. Cell solution was transferred to a 12-well plate. When the 12-well plate was full, the supernatant was taken out, whether the clone was positive is detected with ELISA. The highly expressed positive clones continued to be expanded and frozen, wherein, the protein expression quantities of 3G12, 3C5 and 9G12 strains were high, and 3C5 strain were all high, wherein, the protein expression quantity of 3C5 is maximum.

Example 4: Domestication of CHO-K1 Cell Strains into Suspension Culture (1) Preparation: Ultraviolet sterilization for 30 min in a biosafety cabinet; DMEM/F12 (containing 10% of serum, 25 μM MSX) was preheated to 37° C. in a 37° C. water bath pot.

(2) Cells (10 cm cell culture dish) were taken out from a 37° C. incubator, the supernatant culture medium was discarded, the cells were washed once with 8 mL of PBS, and the PBS was discarded.

(3) 1-2 mL of 0.25% trypsin-EDTA was added to each 10 cm cell culture dish and digested at room temperature for about 2 min. Cells were observed to be shrunk and become round under a microscope, showing a single cell.

(4) 4 mL of DMEM/F12 (containing 10% of serum, 25 μM MSX) was added to end the digestive reaction and the cells were dispersed with a pipette gun.

(5) The digested cells were transferred to a 15 mL centrifugal tube and centrifuged for 5 min at 200 g under room temperature.

(6) Cells were suspended with 100% DMEM/F12 (containing 10% of serum, 25 μM MSX) and counted.

(7) The cells were diluted to $5\times10^5$ cells/mL to be inoculated to 30 mL culture medium in a 125 mL shaking flask. Cell culture flasks were placed on an orbital oscillator in 37° C., 5% $CO_2$ cell incubator to be incubated at 120 rpm/min for overnight.

(8) The surface of the biosafety cabinet was wiped and sterilized with 75% alcohol and subjected to ultraviolet radiation for 30 minutes.

(9) Cell density and viability were counted every 24 hours.

(10) When the survival rate of the first generation cells reached 94-97% after they are cultured once, the second-generation cells were cultured.

(11) Preparation: Ultraviolet sterilization for 30 min in a biosafety cabinet; 100% DMEM/F, 12 (containing 10% of serum, 25 μM MSX) and EX-CELL 302 were preheated to 37° C. in a 37° C., $CO_2$ cell incubator.

(12) Cells were taken out from the 37° C. incubator and transferred to 50 mL centrifugal tube, and the centrifugal tube was centrifuged for 5 min at 200 g under room temperature.

(13) DMEM/F12 (containing 10% of serum, 25 μM MSX) and EX-CELL 302 were mixed in a ratio of 1:1 and MSX having a corresponding concentration was added to be uniformly mixed. The cells were re-suspended and counted.

(14) Cells were diluted to $5\times10^5$ cells/mL to be inoculated in 30 mL culture medium in a 125 mL shaking flask. Cell culture flasks were placed an orbital oscillator in 37° C., 5% $CO_2$ cell incubator to be incubated at 120 rpm/min for overnight.

(15) The surface of the biosafety cabinet was wiped and sterilized with 75% alcohol and subjected to ultraviolet radiation for 30 min.

(16) Cell density and viability were counted every 24 hours.

(17) The survival rate of the cells obtained after the second-generation culture was carried out twice was larger than 95%; the survival rate of the cells obtained after the third to sixth-generation culture was carried out three times was larger than 95%. After 7 weeks, three generations of cells were propagated after 3 days of inoculation, with a density of $1\times10^6$ cells/mL and a cell survival rate of 95%. It was considered that the cells had been adapted to suspension culture. The inoculation density was reduced to $3\times10^5$ cells/mL.

(18) After domestication, 3G12 strains and 3C5 strains both satisfied requirements, indicating domestication of 3G12 strains and 3C5 strains was successful.

Example 5: Shaking Flask Fermentation of Cells (3C5 Strains were Fermented as an Experiment Subject)

(1) Preparation of passage culture medium (3C5 strains were fermented as an experiment subject): 60% CD-CHO+40% Ex-cell 302 was preheated to 37° C. in a 37° C. water bath pot.

(2) The shaken cells were taken out from a $CO_2$ thermostatic shaker and counted.

(3) The cells were diluted to $2.5\text{-}3.5\times10^5$ cells/mL to be inoculated in a 30 mL culture medium in a 125 mL shaking flask. Cell culture flasks were placed at 37° C., 5% CO2 isothermal shaker to be incubated for overnight at 100 rpm/min.

(4) Cell density and viability were counted every 24 hours, and glucose was measured. When glucose was below 2 g/L, glucose was added to 4 g/L; 1 mL of samples was taken every day, and the supernatant was used to detect protein expression.

(5) Supplement (about 4d): 70 g/L CB5 was supplemented, and 10% of basic culture medium was added.

(6) Starting from the 5th day, the temperature of $CO_2$ isothermal shaker was adjusted to 32° C.

(7) On the ninth day, 70 g/L CB5 was supplemented and 10% of the basic medium was added.

(8) On the twelfth day, the supernatant of cells was collected.

Example 6: Purification of Protein

Cell culture liquid was collected and centrifuged for 30 min at 8,000 g under 4° C., the supernatant was taken and passed through a 0.8 m filter membrane, loaded, 80 μL samples were reserved and added into 20 μL of 5×SDS-sample buffer for SDS-PAGE detection.

Column equilibrium: 2-3 CV (column volume) super-pure water equilibrium, and ethanol preservation solution was discharged; then Buffer A (20 mM NaH2PO4 (pH 7.4), 500 mM NaCl) was used to be balanced by 2-3 CV for 4-7 mL/min.

Loading: if a 5 mL pre-packed column is used, loading was carried out at 1 mL/min (the flow rate of loading was adjusted according to the volume of the pre-packed column, and the retention time was 5 min). Flow through (FT) was collected, and the 80 µL of sample was taken and added into 20 µL of 5×SDS-sample buffer for SDS-PAGE detection.

Washing: the column was washed with 4% buffer B (20 mM NaH2PO4 (pH 7.4), 500 mM NaCl, 20 mM imidazole) at a flow rate of 4 mL/min. The unbounded proteins and hybrid proteins with weak binding ability were washed clean until the OD280 nm baseline was stable.

Elution: 50% buffer B (20 mM NaH2PO4 (pH 7.4), 500 mM NaCl, 250 mM imidazole) was used to elute the target protein at 2 mL/min until the baseline was eluted to be flat; collection: 10 mL/tube; after collected samples were mixed (Elutethrough-ET), 80 µL of samples were taken and added to 20 µL 5×SDS-sample buffer for SDS-PAGE detection. See FIG. 4.

Washing: 100% buffer B (20 mM NaH2PO4 (pH 7.4), 500 mM NaCl, 500 mM imidazole), 4 mL/min, no collection, washing 2-3 column volumes until UV baseline is flat. Balance was performed by 2~3 CV with ultra pure water. HisTrap excel column can be preserved to be balanced by 2~3 CV with 20% ethanol solution.

Dialysis and solution change: the imidazole eluent containing the target protein was poured into a dialysis bag to be dialyzed by at least 1,000 folds with 1×PBS, and 80 µl of sample was taken for detection.

Sterilization and filtration: in the biosafety cabinet, the sample passed through a 0.22 µm low protein binding needle filter or a Nalgene filter with 0.22 micron filtration member sterilized by a large amount of protein solution. The filtered protein solution sample is stored in a −80° C. refrigerator.

Figure 4:
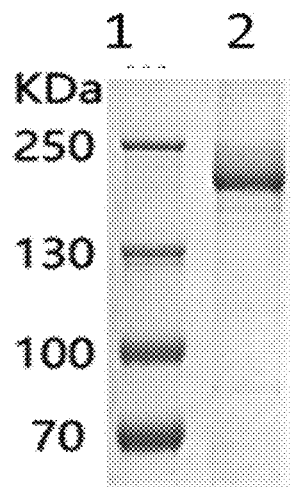
FIG. 4 shows a purification result of a PEDV-S protein expressed by fermentation of a 3C5 monoclonal cell strain detected by SDS-PAGE. Fermentation verification is carried out on the 3C5 monoclonal cell strain, cell culture supernatant is collected, protein purification is performed, and the protein expression level of PEDV-S is detected by SDS-PAGE.

Determination of protein concentration and purity: protein concentration was determined by using a BCA method, and then the yield of protein was calculated according to the volume of supernatant used when in purification and the total amount of proteins obtained after purification. For example, the cell supernatant used in this example was 250 ml in volume, the volume of the purified protein was 250 ml, the concentration was 1050 µg/ml, and the protein yield was about 1 g/L by calculation. The purities were detected by using a HPLC method, and all can reach 90% or more. As shown in FIG. 4 (6% separating gum), the expression yield of 3C5 strains can reach about 1 g/L via detection of SDS-PAGE, and the 3C5 strains were suitable for large-scale production.

Example 7: Detection of Purified PEDV-S Protein 7.1 Deglycosylation, SDS-PAGE Detection and Western Blot Detection of Purified PEDV-S Protein (1) 9 µl of purified PEDV-S protein (about 3 µg) was taken and added into 200 µl EP tube, and 1 µl of 10× glycoprotein degeneration buffer (commercial enzyme self contained a reagent) was added.

(2) The above mixture was boiled for 10 min at 100° C. so that the protein is degenerated.

(3) 2 µl 10×G7 buffer (commercial enzyme self-contained the reagent), 2 µl of 10% NP-40 (commercial enzyme self-contained reagent) and 1-2 µl of PNGaseF (glycosidase F) were added, and water was supplemented, so that the volume of the reaction system reached 20 µl.

(4) Incubation was carried out at 37 C for 1 h.

(5) After the reaction is ended, 5 µl of 5× loading buffer was added, and the mixture was boiled for 10 min for standby.

(6) Deglycosylated proteins were detected by SDS-PAGE. The results are as showed in FIG. 5A (8% separation gel): the molecular weight of purified PEDV-S protein was about 210 kDa. However, after the PEDV-S protein was digested with deglycosylase, it was found that the molecular weight of the deglycosylated PEDV-S protein was only about 140 kDa, which was consistent with the molecular weight, which is about 143 kDa, of the S protein analyzed by the amino acid sequence of the S protein. This result showed that the PEDV-S protein expressed by using our CHO eukaryotic expression system had a large amount of glycosylated modification which accounted for about 33.3% of the total molecular weight of PEDV-S protein. Therefore, when considering the S protein or truncated protein or core region of the S protein was expressed and used for preparation of a vaccine, the glycosylated modification of the expression system must be considered, otherwise the immunogenicity and immune effect of the vaccine will be affected.

Figure 5A:
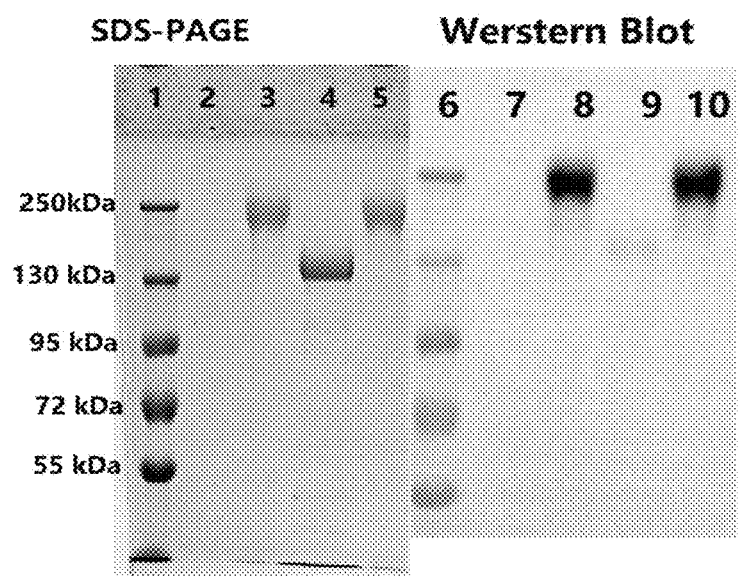
FIG. 5A shows results of deglycosylation of purified PEDV-S protein detected by SDS-PAGE and Western Blot. 1-5 are SDS-PAGE detection results, 1 is Marker, 2 is negative control 1×PBS, 3 and 5 are non-deglycosylated PEDV-S proteins, and 4 is deglycosylated PEDV-S protein; 6-10 are Western Blot results, 6 is Marker, 7 is negative control 1×PBS, 8 and 10 are non-deglycosylated PEDV-S proteins, and 9 is deglycosylated PEDV-S protein.

(7) The deglycosylated proteins were detected by Western Blot. A primary antibody used PEDV pig high immune serum (1:100 fold diluted and then incubated at room temperature for 1 h), the second antibody used sheep anti-pig second antibody (1:5000 fold diluted and then incubated at room temperature for 1 h), and finally ECL was used for color developing. The result is as shown in FIG. 5A (8% separation gel): the deglycosylated PEDV-S protein can not bind to PEDV pig high immune serum or weakly binds to PEDV pig high immune serum, indicating that glycosylation of the PEDV-S protein is essential for maintaining the immunogenicity of PEDV-S protein.

7.2 Molecular Sieve Analysis of Purified PEDV-S Protein 7.2.1 Superdex 200 PG Column Equilibrium Ultra-pure water was used to balance two column volumes, and the ethanol preservation solution was discharged. Then two column volumes were balanced with a mobile phase. The flow rate was 1 mL/min, and the pressure was controlled within 0.5 MPa.

7.2.2 Injection 2 mL of PEDV-S protein (concentration is 3.153 mg/mL) was injected with an injection ring at a flow rate of 1 mL/min and the pressure was controlled to 0.5 MPa.

1.6.3 Operation

After injection was completed, the inject state was changed to a load state, and operation was carried out at the flow rate of 1 mL/min. After peaks occurred, the sample was collected with 0.5 mL/tube.

Figure 5B:
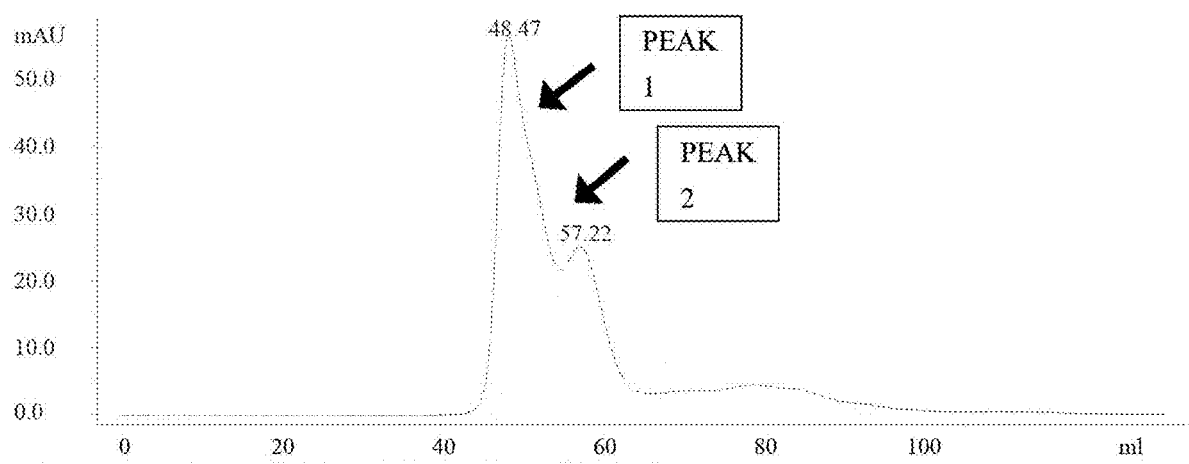
FIG. 5B shows a molecular sieve detection result of PEDV-S protein.
Figure 5C:
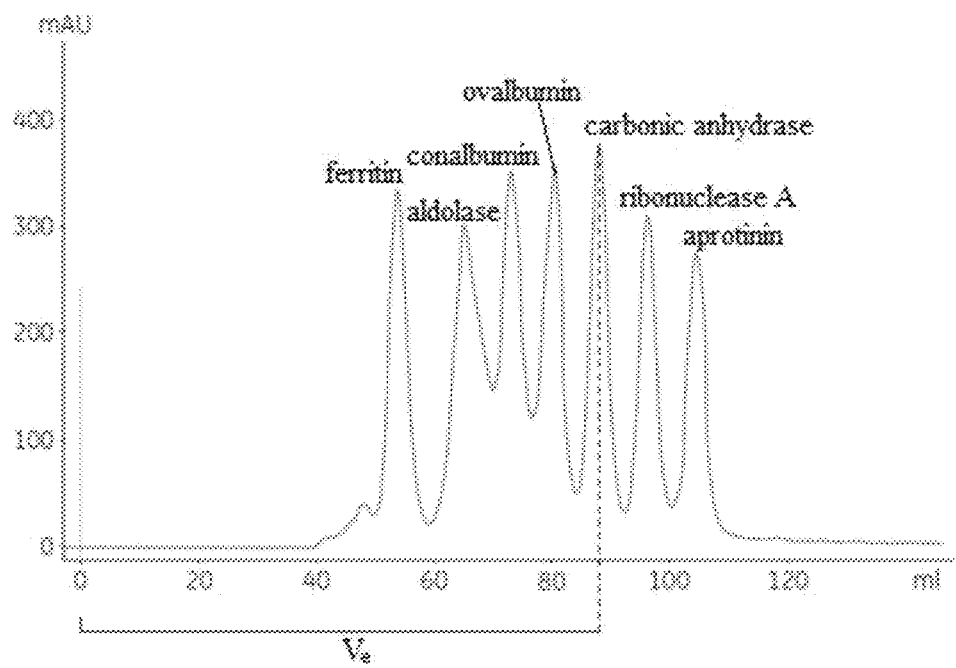
FIG. 5C shows a chromatogram of a superdex 200 PG column standard sample, in which the ferritin peak volume is 54.1 ml, the molecular weight is 440 kDa, the aldolase peak volume is 65.4 ml, the molecular weight is 158 kDa, the conalbumin peak volume is 73.0 ml, the molecular weight is 75 kDa, the ovalbumin peak volume is 80.0 ml, the molecular weight is 43 kDa, the carbonic anhydrase peak volume is 87.9 ml, the molecular weight is 29 kDa, the ribonuclease A peak volume is 95.7 ml, t hmolecular weight is 13.7 kDa, the aprotinin peak volume is 104.3 ml and the molecular weight is 6.5 kDa.
Figure 6:
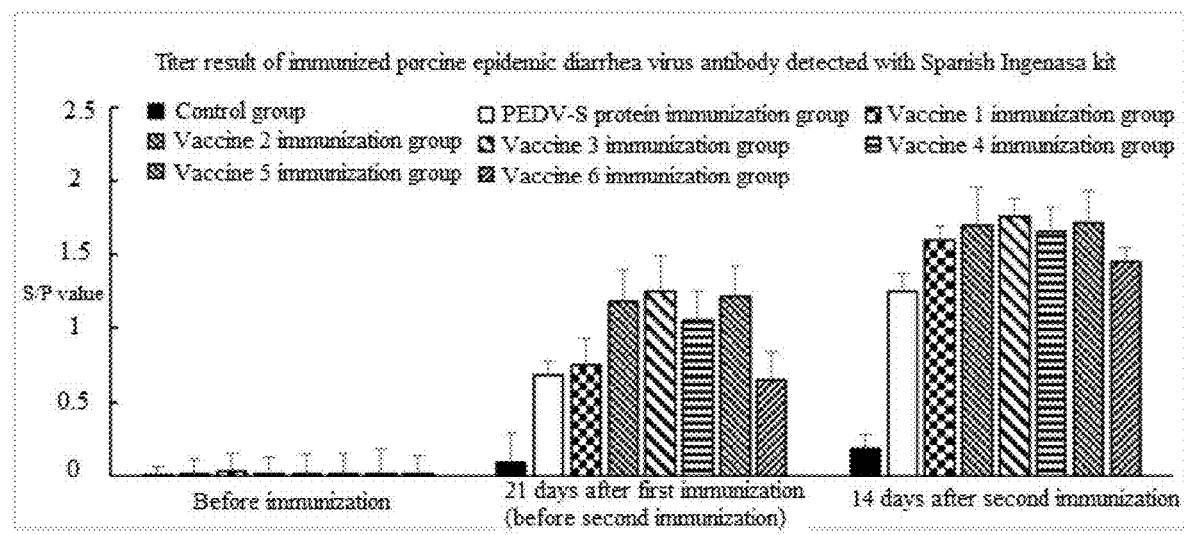
FIG. 6 shows a titer detection result after immunization.

Molecular sieve results were as shown in FIG. 5B: it can be seen from comparison of the PEDV-S protein molecular sieve peak result with a standard column chromatogram (FIG. 5C) that the volume of peak 1 was 48.47 ml, the molecular weight of peak 1 was more than 440 kDa, and thus peak 1 represented a trimer of purified PEDV-S protein; the volume of peak 2 was 57.22 ml, and the molecular weight of peak 2 was between 158 kDa and 440 kDa, and thus peak 2 represented a monomer of PEDV-S protein; and the molecular weights of proteins corresponding to other peaks were all less than 158 kDa and hybrid proteins.

As can be seen from the drawing that the area (302.6616) of peak 1 accounts for 69% of the total area (438.5518), indicating that 69% of purified PEDV-S protein is the trimer before the buffer system was not further optimized, which met predictive analysis (PEDV-S protein existed in the form of the trimer in a PEDV virus particle).

Example 8: Preparation of Vaccines and Immunological Experiment 8.1 Preparation of Vaccines (Take 2 ml/Vaccine, Total 200 ml as an Example)

The consumables and materials used to prepare vaccines were all needed to be sterilized in advance. The preparation process was completed in a biosafety cabinet or other instruments or environments that can ensure the sterilization of the whole preparation process.

(1) Preparation of oil phase (ISA 201 VG adjuvant): according to a volume ratio of water phase to oil phase of 46:54, 108 ml of oil phase was weighed to be placed in a reagent bottle prepared in advance, sealed and then preheated for about 30 min in a 33° C. water bath pot.

(2) Preparation of water phase: according to a volume ratio of water phase to oil phase of 46:54, the total volume of the water phase is 92 ml.

The volume of the used S protein was calculated according to the concentration of the porcine epidemic diarrhea virus S protein and the concentration of the S protein in the vaccine; if the immuopotentiator Quil-A was also added in the water phase, the volume of the used Quil-A was calculated according to the original concentration of Quil-A and the content of Quil-A in the vaccine; the total volume of the water phase was supplemented to 92 ml with PBS or other buffer solution, and then the water phase was uniformly mixed and preheated for about 30 min in a 33° C. water bath pot. For example, the concentration of PEDV-S protein was 5 mg/ml and the original concentration of Quil-A was 10 mg/ml. The particular preparation was shown in a table below.

| Volume | Vaccine 1 ( total protein concentration 15 μg/ml: Quil-A 200 μg/ml) | Vaccine 2 ( total protein concentration 50 μg/ml: Quil-A 200 μg/ml) | Vaccine 3 (total protein concentration 100 μg/ml: Quil-A 200 μg/ml) |
|---|---|---|---|
| PEDV-S | 0.6 ml | 2 ml | 4 ml |
| Quil-A | 4 ml | 4 ml | 4 ml |
| PBS | 87.4 ml | 86 ml | 84 ml |
| Total volume | 92 ml | 92 ml | 92 ml |

| Volume | Vaccine 2 ( total protein concentration 50 μg/ml: Quil-A 200 μg/ml) | Vaccine 4 ( total protein concentration 50 μg/ml: Quil-A 150 μg/ml) | Vaccine 5 (total protein concentration 50 μg/ml: Quil-A 250 μg/ml) | Vaccine 6 (total protein concentration 50 μg/ml: Quil-A 0 μg/ml) |
|---|---|---|---|---|
| PEDV-S | 2 ml | 2 ml | 2 ml | 2 ml |
| Quit-A | 4 ml | 3 ml | 5 ml | 0 ml |
| PBS | 86 ml | 87 ml | 85 ml | 90 ml |
| Total volume | 92 ml | 92 ml | 92 1 | 93 1 |

(3) Stirring: the preheated oil phase was added into a prepared beaker, the height and speed of a mixer were adjusted, then the preheated water phase was quickly added to the oil phase, and stirring was continued for 10-20 min. Generally, the stirring speed and stirring time were chosen according to the volume of preparation, for example, 200 ml of vaccine was generally prepared by selecting the stirring speed of 350 rpm/min and stirring time of 10 min, or 1500 ml of vaccine was typically prepared by selecting the stirring speed of 600 rpm/min and stirring time of 20 min.

(4) Stabilization: the vaccine stirred in (3) was put in a 20° C. water bath pot and stood for 1 h, and then put in a 4° C. refrigerator for overnight.

(5) Sub-package: the stabilized vaccines were sub-packaged and labeled as needed.

8.2 Preparation of PEDV-S1 protein according to invention patent with Chinese patent application number 201610348237.8, and then the vaccine was prepared according to the method in 8.1. In addition to PEDV-S1 protein, the other components and concentrations of this vaccine and the prepared vaccine in 8.1 were completely the same, that is, the concentration of PEDV-S1 protein in this vaccine was 100 μg/vaccine, the concentration of Quil-A was 400 μg/vaccine, and the volume ratio of the adjuvant to the water phase was 54:46.

8.3 Immunological Experiment

Forty piglets aged 28-35 days (PEDV, TGEV and RV antigen negative, PEDV antibody negative) were screened and randomly divided into five groups, and each group had 5 piglets. One group served as a blank control group, six groups were immunized with PEDV-S protein subunit vaccines (vaccines 1-6 prepared in 8.1), and one group was immunized with PEDV-S1 protein subunit vaccine (the vaccine prepared in 8.2). The blank control group was injected with 2 ml of saline intramuscularly each time and the immunization group was injected with 2 ml of corresponding vaccine intramuscularly each time. The immunization was strengthened once after three weeks of preliminary immunization. Serums were collected before immunization, before secondary immunization and 14 days after secondary immunization. The titer of the antibody was detected by indirect ELISA kit of Spanish Ingenasa porcine epidemic diarrhea virus.

The results are shown in FIG. 6:

(1) The average S/P value of vaccination group 2 (containing PEDV-S protein) can reach about 1.1 21 days after first immunization, and can reach 1.7 14 days after second immunization, while the average S/P value of PEDV-S1 protein vaccination group was only about 0.7 21 days after first immunization, and only about 1.2 14 days after second immunization. This indicates that the immunogenicity of full-length PEDV-S is better than that of PEDV-S1.

(2) After vaccines (namely vaccine 1-vaccine 3) prepared with PEDV-S proteins having different concentrations are immunized, the S/P value after first immunization increase with the rising of concentration, but the S/P value of vaccine 1 can also reach 1.1 or more which is higher than that of PEDV-S1 protein immunization group, while after second immunization, the S/P values of three groups of vaccines are basically the same and all between 1.7 and 0.1, which indicates that the concentration of PEDV-S protein in vaccines hardly influences second immunization, and slightly influences first immunization, but it can achieve the protective effect.

(3) the S/P values of vaccines (i.e. vaccine 2, vaccine 4-vaccine 6) prepared with Quil A having different concentrations increase with the rising of the concentrations, but they are about 0.4 higher than the average S/P values of vaccines without Quil A (the average S/P value of vaccine 6 were about 0.6 after first immunization, and the average S/P values of vaccine 4 were above 1.0 after first immunization); after second immunization, the S/P values of three groups of vaccines (vaccines 1, 4 and 5) containing Quil A are basically the same and all about 1.7, and are not more than 0.2~0.3 (the average S/P of vaccine 6 after second immunization is only about 1.4); it indicates that Quil A in vaccines has a very good enhancement effect on immunization, especially for first immunization, and this is a good complement for quick generation of immune protection of vaccines.

Example 9: Clinic Large-Scale Immunological Experiment (1) Pig farms and immunization situations: this experiment was used for three pig farms from September to November 2017: 1100 sows for A pig farm and 700 sows for B pig farm. Sows were immunized for the first time 40 days before delivery and immunized for the second time 20 days before delivery. Each immunization dose was 2 ml/vaccine, and the immunization vaccine was made as vaccine 6 in example 8, all of which were injected into neck muscles.

(2) Clinical Observation Results

A farm: it was well managed. No diarrhea cases occurred from 2016 to 2017. After the sows were administrated with PEDV subunit vaccine, swinery was in normal condition and there was no diarrhea in sows and piglets.

B farm: the incidence of diarrhea was serious in winter 2016. It was estimated that 3000 newborn piglets died in one year. No diarrhea cases occurred in sows and piglets after PEDV subunit vaccine was used. Similarly, the death of piglets caused by diarrhea was prevented.

The disclosure is exemplified by the above examples. However, it is understood that the disclosure is not limited to the described special examples and embodiments. Here, these special examples and embodiments are intended to help those skilled in the art to implement the disclosure. Any improvements and perfections are made by those skilled in the art without departing from the spirit and scope of the disclosure, and therefore the disclosure is only limited by contents and scope of claims of the disclosure and intended to cover alternative solutions and equivalent solutions included within the spirit and scope of the disclosure defined by appended claims.

We claim:

1. A porcine epidemic diarrhea virus S protein, having an amino acid sequence of SEQ ID NO:2, and a molecular weight of 210 kDa, wherein
the porcine epidemic diarrhea virus S protein is expressed by CHO cells and has a glycosylated modification accounting for 33.3% of the molecular weight thereof.

2. A porcine epidemic diarrhea virus S protein subunit vaccine, the vaccine comprising: the porcine epidemic diarrhea virus S protein according to claim 1 and a pharmaceutically acceptable ISA 201 VG adjuvant, wherein the porcine epidemic diarrhea virus S protein has a concentration of 30-200 μg/vaccine.

3. The vaccine according to claim 2, the vaccine further comprising an immunopotentiator, wherein the immunopotentiator is Quil A having a concentration of 300-500 μg/vaccine.

4. A method for preparing a vaccine comprising the porcine epidemic diarrhea virus S protein according to claim 1, the method comprising the following steps:
(1) cloning an OPTI-S having a nucleotide sequence of SEQ ID NO:1, comprising:
1-1) performing codon optimization on a PEDV-S having a nucleotide sequence of SEQ ID NO:3 to obtain the OPTI-S; and
1-2) cloning the OPTI-S to an eukaryotic expression vector to obtain a recombinant plasmid;

(2) expressing and purifying the porcine epidemic diarrhea virus S protein; the expressing and purifying the porcine epidemic diarrhea virus S protein comprising the following steps:
2-1) transfecting the recombinant plasmid to a CHO cell strain;
2-2) culturing, screening and acclimating the CHO cell strain in step 2-1) to obtain a highly-expressed cell strain; and
2-3) performing fermentation culture on the cell strain in step 2-2), and purifying the supernatant of the cell to obtain the porcine epidemic diarrhea virus S protein;
(3) preparing the porcine epidemic diarrhea virus S protein into a water phase; and
(4) emulsifying the water phase and an ISA 201 VG adjuvant as an oil phase in a volume ratio of 46:54 to obtain the vaccine.

5. The method according to claim 4, wherein the water phase further comprises an immunopotentiator which is Quil-A.

6. The method according to claim 4, wherein the eukaryotic expression vector is pEE12.4.

7. The method according to claim 4, wherein the CHO cell is a CHO-K1 cell.

8. The porcine epidemic diarrhea virus S protein according to claim 1, wherein the porcine epidemic diarrhea virus S protein is encoded by a nucleotide sequence of SEQ ID NO: 1.

9. A polynucleotide for encoding the porcine epidemic diarrhea virus S protein according to claim 1, having a nucleotide sequence of SEQ ID NO: 1.

* * * * *

SEQUENCE LISTING

```
<160> NUMBER OF SEQ ID NOS: 3

<210> SEQ ID NO 1
<211> LENGTH: 3909
<212> TYPE: DNA
<213> ORGANISM: Artificial Sequence
<220> FEATURE:
<223> OTHER INFORMATION: Synthesized

<400> SEQUENCE: 1
gacgtgacca ggtgctctgc caacacaaat ttcaggcggt tctttagcaa gtttaacgtg      60
caggctccag ctgtggtggt gctgggagga tacctgccaa tcggcgagaa tcagggcgtg     120
aactctacat ggtattgtgc tggacagcac cctaccgcta gcggagtgca tggcatcttc     180
gtgtcccaca tcaggggcgg ccatggcttc gagatcggca tctcccagga gcccttgac      240 cctagcggct accagctgta tctgcacaag gccaccaacg gcaataccaa cgccacagct     300
agactgcgca tctgccagtt cccctctatc aagaccctgg gccctacagc taacaatgat     360
gtgaccacag gccggaattg tctgtttaac aaggccatcc cagctcacat gagcgagcat     420
tctgtggtgg gcatcacctg ggacaacgat agagtgacag tgttctccga caagatctac     480
tatttctact ttaagaacga ttggagccgc gtggccacca agtgctataa ttctggcggc     540
tgtgctatgc agtacgtgta tgagccaacc tactatatgc tgaatgtgac atctgccgga     600
gaggacggaa tctcctacca gccatgcaca gccaattgta tcggctatgc cgctaacgtg     660
ttcgctaccg agcctaatgg ccacatccca gagggcttct cttttaacaa ttggttctg      720 ctgtccaacg atagcaccct ggtgcatggc aaggtggtgt ccaatcagcc tctgctggtg     780
aactgcctgc tggctatccc aaagatctac ggcctgggcc agttcttttc cttcaaccag     840
acaatcgacg gcgtgtgcaa tggagctgct gtgcagaggg ctccagaggc tctgcggttt     900
aatatcaacg ataccagcgt gatcctggcc gagggctcta tcgtgctgca caccgctctg     960
ggcacaaact tctccttcgt gtgctccaat tccagcgacc cccatctggc caccttcgct    1020
atcccactgg gcgccatcca ggtgccctac tattgtttcc tgaaggtgga tacctacaac    1080
agcacagtgt ataagtttct ggctgtgctg ccccctaccg tgagggagat cgtgatcaca    1140
aagtacggcg acgtgtatgt gaacggcttc ggctacctgc acctgggcct gctggatgcc    1200
gtgaccatca acttcaccgt gcatggcacc gacgatgacg tgtccggctt ctggacaatc    1260
```

```
gccagcacca actttgtgga cgctctgatc gaggtgcagg gcaccgccat ccagagaatc   1320
ctgtactgcg atgacccegt gtcccagctg aagtgtagcc aggtggcttt cgacctggat   1380
gacggctttt atccaatctc ttcccgcaat ctgctgtccc acgagcagcc tatcagcttc   1440
gtgacactgc catctttcaa tgatcactcc tttgtgaaca tcaccgtgtc cgcctccttc   1500
ggcggacatt ctggagccaa cctgatcgct tccgacacca caatcaatgg cttcagctct   1560
ttttgcgtgg atacaagaca gttcaccatc tccctgtttt acaatgtgac aaacagctac   1620
ggctacgtgt ccaagagcca ggactctaac tgtcccttca ccctgcagtc cgtgaatgat   1680
tatctgtctt tctccaagtt ttgcgtgagc acctctctgc tggcctccgc ttgtacaatc   1740
gatctgttcg gctaccctga gtttggctct ggcgtgaagt ttacctccct gtatttccag   1800
tttacaaagg gcgagctgat caccggcaca ccaaagcccc tggagggcgt gaccgacgtg   1860
agcttcatga cactggacgt gtgcaccaag tacacaatct atggctttaa gggcgagggc   1920
atcatcaccc tgacaaactc cagcttcctg gccggctttt actatacatc cgacagcggc   1980
cagctgctgg ccttcaagaa tgtgaccagc ggcgccgtgt actctgtgac accctgttct   2040
ttttccgagc aggccgctta tgtggatgac gatatcgtgg gcgtgatctc ttccctgagc   2100
aattctacat tcaacagcac cagagagctg cccggcttct tttaccatag caatgatggc   2160
tctaactgca ccgagcctgt gctggtgtac tccaacatcg gcgtgtgcaa gtccggcagc   2220
atcggctatg tgccaagcca gccaggacag gtgaagatcg ctccaaccgt gacaggcaat   2280
atctctatcc ctaccaactt ttctatgtcc atccgcacag agtacctgca gctgtataac   2340 acaccegtga tcgtggactg cgctacctac gtgtgcaacg gcaattccag atgcaagcag   2400
ctgctgaccc agtatacagc cgcttgtaag accatcgagt ctgccctgca gctgtccgct   2460
aggctggaga gcgtggaggt gaactctatg ctgacaatct ccgaggagag cctgcagctg   2520
gccaccatct ccagcttcaa tggcggcggc tacaactttta ccaatgtgct gggcgtgtcc   2580
gtgtatgacc ctgctagcgg cagagtggtg cagaagcgca gcttcatcga ggatctgctg   2640
tttaacaagg tggtgaccaa tggcctgggc acagtggacg aggattacaa gaggtgcagc   2700
aacggccggt ctgtggctga cctggtgtgc gctcagtact attctggcgt gatggtgctg   2760
ccaggcgtgg tggatgccga aagctgcac atgtattccg cctccctgat cggaggaatg   2820
gtgctgggag gcttcacaag cgccgctgcc ctgcccttttt cttacgctgt gcaggccaga   2880
ctgaactatc tggccctgca gaccgacgtg ctgcagagga tcagcagct gctggccgag   2940 tctttcaact ccgctatcgg caatatcaca tccgccttttg agagcgtgaa ggagtccatc   3000
agccagacca gcaagggcct gaacacagtg gctcacgccc tgaccaaggt gcaggaggtg   3060
gtgaactccc agggagctgc cctgacccag ctgacagtgc agctgcagca taacttccag   3120
gccatctctt ccagcatcga cgatatctac tctagactgg atatcctgtc cgctgacgtg   3180
caggtggata gactgatcac aggccgcctg tccgctctga cgcctttgt ggctcagacc   3240 ctgacaaagt acaccgaggt gcaggccagc aggaagctgg ctcagcagaa agtgaatgag   3300
tgcgtgaagt ctcagtccca gcggtatggc ttctgtggcg gcgacggcga gcacatcttt   3360
tccctggtgc aggctgctcc acagggactg ctgttcctgc ataccgtgct ggtgcctggc   3420
gactttgtgg atgtgatcgc tatcgccggc ctgtgcgtga cgatgagat cgccctgaca   3480 ctgagggagc ctggactggt gctgttcacc cacgagctgc agaatcatac cgctacagag   3540
tacttcgtgt cttccaggcg gatgtttgag cccaggaagc ctaccgtgtc cgactttgtg   3600
```

-continued

```
cagatcgaga gctgcgtggt gacctacgtg aacctgacac gggaccagct gcctgatgtg    3660
atcccagact atatcgatgt gaacaagaca ctggatgaga tcctggcctc tctgccaaat    3720
aggaccggac catccctgcc actggacgtg ttcaacgcca cctatctgaa tctgacaggc    3780
gagatcgctg atctggagca gaggagcgag tctctgcgga acaccacaga ggagctgcag    3840
tccctgatct acaatatcaa caatacactg gtggatctgg agtggctgaa tcgggtggag    3900
acctatatc                                                            3909
```

<210> SEQ ID NO 2
<211> LENGTH: 1303
<212> TYPE: PRT
<213> ORGANISM: Artificial Sequence
<220> FEATURE:
<223> OTHER INFORMATION: Synthesized

<400> SEQUENCE: 2

```
Asp Val Thr Arg Cys Ser Ala Asn Thr Asn Phe Arg Arg Phe Phe Ser
1               5                   10                  15

Lys Phe Asn Val Gln Ala Pro Ala Val Val Leu Gly Gly Tyr Leu
            20                  25                  30

Pro Ile Gly Glu Asn Gln Gly Val Asn Ser Thr Trp Tyr Cys Ala Gly
        35                  40                  45

Gln His Pro Thr Ala Ser Gly Val His Gly Ile Phe Val Ser His Ile
    50                  55                  60

Arg Gly Gly His Gly Phe Glu Ile Gly Ile Ser Gln Glu Pro Phe Asp
65                  70                  75                  80

Pro Ser Gly Tyr Gln Leu Tyr Leu His Lys Ala Thr Asn Gly Asn Thr
                85                  90                  95

Asn Ala Thr Ala Arg Leu Arg Ile Cys Gln Phe Pro Ser Ile Lys Thr
            100                 105                 110

Leu Gly Pro Thr Ala Asn Asn Asp Val Thr Thr Gly Arg Asn Cys Leu
        115                 120                 125

Phe Asn Lys Ala Ile Pro Ala His Met Ser Glu His Ser Val Val Gly
    130                 135                 140

Ile Thr Trp Asp Asn Asp Arg Val Thr Val Phe Ser Asp Lys Ile Tyr
145                 150                 155                 160

Tyr Phe Tyr Phe Lys Asn Asp Trp Ser Arg Val Ala Thr Lys Cys Tyr
                165                 170                 175

Asn Ser Gly Gly Cys Ala Met Gln Tyr Val Tyr Glu Pro Thr Tyr Tyr
            180                 185                 190

Met Leu Asn Val Thr Ser Ala Gly Glu Asp Gly Ile Ser Tyr Gln Pro
        195                 200                 205

Cys Thr Ala Asn Cys Ile Gly Tyr Ala Ala Asn Val Phe Ala Thr Glu
    210                 215                 220

Pro Asn Gly His Ile Pro Glu Gly Phe Ser Phe Asn Asn Trp Phe Leu
225                 230                 235                 240

Leu Ser Asn Asp Ser Thr Leu Val His Gly Lys Val Val Ser Asn Gln
                245                 250                 255

Pro Leu Leu Val Asn Cys Leu Leu Ala Ile Pro Lys Ile Tyr Gly Leu
            260                 265                 270

Gly Gln Phe Phe Ser Phe Asn Gln Thr Ile Asp Gly Val Cys Asn Gly
        275                 280                 285

Ala Ala Val Gln Arg Ala Pro Glu Ala Leu Arg Phe Asn Ile Asn Asp
    290                 295                 300
```

-continued

```
Thr Ser Val Ile Leu Ala Glu Gly Ser Ile Val Leu His Thr Ala Leu
305                 310                 315                 320
Gly Thr Asn Phe Ser Phe Val Cys Ser Asn Ser Ser Asp Pro His Leu
            325                 330                 335
Ala Thr Phe Ala Ile Pro Leu Gly Ala Ile Gln Val Pro Tyr Tyr Cys
                340                 345                 350
Phe Leu Lys Val Asp Thr Tyr Asn Ser Thr Val Tyr Lys Phe Leu Ala
        355                 360                 365
Val Leu Pro Pro Thr Val Arg Glu Ile Val Ile Thr Lys Tyr Gly Asp
    370                 375                 380
Val Tyr Val Asn Gly Phe Gly Tyr Leu His Leu Gly Leu Leu Asp Ala
385                 390                 395                 400
Val Thr Ile Asn Phe Thr Val His Gly Thr Asp Asp Val Ser Gly
                405                 410                 415
Phe Trp Thr Ile Ala Ser Thr Asn Phe Val Asp Ala Leu Ile Glu Val
                420                 425                 430
Gln Gly Thr Ala Ile Gln Arg Ile Leu Tyr Cys Asp Asp Pro Val Ser
            435                 440                 445
Gln Leu Lys Cys Ser Gln Val Ala Phe Asp Leu Asp Asp Gly Phe Tyr
    450                 455                 460
Pro Ile Ser Ser Arg Asn Leu Leu Ser His Glu Gln Pro Ile Ser Phe
465                 470                 475                 480
Val Thr Leu Pro Ser Phe Asn Asp His Ser Phe Val Asn Ile Thr Val
                485                 490                 495
Ser Ala Ser Phe Gly Gly His Ser Gly Ala Asn Leu Ile Ala Ser Asp
                500                 505                 510
Thr Thr Ile Asn Gly Phe Ser Ser Phe Cys Val Asp Thr Arg Gln Phe
            515                 520                 525
Thr Ile Ser Leu Phe Tyr Asn Val Thr Asn Ser Tyr Gly Tyr Val Ser
    530                 535                 540
Lys Ser Gln Asp Ser Asn Cys Pro Phe Thr Leu Gln Ser Val Asn Asp
545                 550                 555                 560
Tyr Leu Ser Phe Ser Lys Phe Cys Val Ser Thr Ser Leu Leu Ala Ser
                565                 570                 575
Ala Cys Thr Ile Asp Leu Phe Gly Tyr Pro Glu Phe Gly Ser Gly Val
            580                 585                 590
Lys Phe Thr Ser Leu Tyr Phe Gln Phe Thr Lys Gly Glu Leu Ile Thr
    595                 600                 605
Gly Thr Pro Lys Pro Leu Glu Gly Val Thr Asp Val Ser Phe Met Thr
610                 615                 620
Leu Asp Val Cys Thr Lys Tyr Thr Ile Tyr Gly Phe Lys Gly Glu Gly
625                 630                 635                 640
Ile Ile Thr Leu Thr Asn Ser Ser Phe Leu Ala Gly Phe Tyr Tyr Thr
                645                 650                 655
Ser Asp Ser Gly Gln Leu Leu Ala Phe Lys Asn Val Thr Ser Gly Ala
            660                 665                 670
Val Tyr Ser Val Thr Pro Cys Ser Phe Ser Glu Gln Ala Ala Tyr Val
    675                 680                 685
Asp Asp Asp Ile Val Gly Val Ile Ser Ser Leu Ser Asn Ser Thr Phe
690                 695                 700
Asn Ser Thr Arg Glu Leu Pro Gly Phe Phe Tyr His Ser Asn Asp Gly
705                 710                 715                 720
Ser Asn Cys Thr Glu Pro Val Leu Val Tyr Ser Asn Ile Gly Val Cys
```

```
                725                 730                 735
Lys Ser Gly Ser Ile Gly Tyr Val Pro Ser Gln Pro Gly Gln Val Lys
            740                 745                 750
Ile Ala Pro Thr Val Thr Gly Asn Ile Ser Ile Pro Thr Asn Phe Ser
            755                 760                 765
Met Ser Ile Arg Thr Glu Tyr Leu Gln Leu Tyr Asn Thr Pro Val Ile
            770                 775                 780
Val Asp Cys Ala Thr Tyr Val Cys Asn Gly Asn Ser Arg Cys Lys Gln
785                 790                 795                 800
Leu Leu Thr Gln Tyr Thr Ala Ala Cys Lys Thr Ile Glu Ser Ala Leu
            805                 810                 815
Gln Leu Ser Ala Arg Leu Glu Ser Val Glu Val Asn Ser Met Leu Thr
            820                 825                 830
Ile Ser Glu Glu Ser Leu Gln Leu Ala Thr Ile Ser Ser Phe Asn Gly
            835                 840                 845
Gly Gly Tyr Asn Phe Thr Asn Val Leu Gly Val Ser Val Tyr Asp Pro
            850                 855                 860
Ala Ser Gly Arg Val Val Gln Lys Arg Ser Phe Ile Glu Asp Leu Leu
865                 870                 875                 880
Phe Asn Lys Val Val Thr Asn Gly Leu Gly Thr Val Asp Glu Asp Tyr
            885                 890                 895
Lys Arg Cys Ser Asn Gly Arg Ser Val Ala Asp Leu Val Cys Ala Gln
            900                 905                 910
Tyr Tyr Ser Gly Val Met Val Leu Pro Gly Val Val Asp Ala Glu Lys
            915                 920                 925
Leu His Met Tyr Ser Ala Ser Leu Ile Gly Gly Met Val Leu Gly Gly
            930                 935                 940
Phe Thr Ser Ala Ala Ala Leu Pro Phe Ser Tyr Ala Val Gln Ala Arg
945                 950                 955                 960
Leu Asn Tyr Leu Ala Leu Gln Thr Asp Val Leu Gln Arg Asn Gln Gln
            965                 970                 975
Leu Leu Ala Glu Ser Phe Asn Ser Ala Ile Gly Asn Ile Thr Ser Ala
            980                 985                 990
Phe Glu Ser Val Lys Glu Ser Ile Ser Gln Thr Ser Lys Gly Leu Asn
            995                 1000                1005
Thr Val Ala His Ala Leu Thr Lys Val Gln Glu Val Val Asn Ser
            1010                1015                1020
Gln Gly Ala Ala Leu Thr Gln Leu Thr Val Gln Leu Gln His Asn
            1025                1030                1035
Phe Gln Ala Ile Ser Ser Ser Ile Asp Asp Ile Tyr Ser Arg Leu
            1040                1045                1050
Asp Ile Leu Ser Ala Asp Val Gln Val Asp Arg Leu Ile Thr Gly
            1055                1060                1065
Arg Leu Ser Ala Leu Asn Ala Phe Val Ala Gln Thr Leu Thr Lys
            1070                1075                1080
Tyr Thr Glu Val Gln Ala Ser Arg Lys Leu Ala Gln Gln Lys Val
            1085                1090                1095
Asn Glu Cys Val Lys Ser Gln Ser Gln Arg Tyr Gly Phe Cys Gly
            1100                1105                1110
Gly Asp Gly Glu His Ile Phe Ser Leu Val Gln Ala Ala Pro Gln
            1115                1120                1125
Gly Leu Leu Phe Leu His Thr Val Leu Val Pro Gly Asp Phe Val
            1130                1135                1140
```

| | | | | | | | | | | |
|---|---|---|---|---|---|---|---|---|---|---|
| Asp | Val | Ile | Ala | Ile | Ala | Gly | Leu | Cys | Val | Asn | Asp | Glu | Ile | Ala |
| | 1145 | | | | 1150 | | | | 1155 | |

Asp Val Ile Ala Ile Ala Gly Leu Cys Val Asn Asp Glu Ile Ala
       1145                   1150                  1155

Leu Thr Leu Arg Glu Pro Gly Leu Val Leu Phe Thr His Glu Leu
       1160                   1165                  1170

Gln Asn His Thr Ala Thr Glu Tyr Phe Val Ser Ser Arg Arg Met
       1175                   1180                  1185

Phe Glu Pro Arg Lys Pro Thr Val Ser Asp Phe Val Gln Ile Glu
       1190                   1195                  1200

Ser Cys Val Val Thr Tyr Val Asn Leu Thr Arg Asp Gln Leu Pro
       1205                   1210                  1215

Asp Val Ile Pro Asp Tyr Ile Asp Val Asn Lys Thr Leu Asp Glu
       1220                   1225                  1230

Ile Leu Ala Ser Leu Pro Asn Arg Thr Gly Pro Ser Leu Pro Leu
       1235                   1240                  1245

Asp Val Phe Asn Ala Thr Tyr Leu Asn Leu Thr Gly Glu Ile Ala
       1250                   1255                  1260

Asp Leu Glu Gln Arg Ser Glu Ser Leu Arg Asn Thr Thr Glu Glu
       1265                   1270                  1275

Leu Gln Ser Leu Ile Tyr Asn Ile Asn Asn Thr Leu Val Asp Leu
       1280                   1285                  1290

Glu Trp Leu Asn Arg Val Glu Thr Tyr Ile
       1295                   1300

<210> SEQ ID NO 3
<211> LENGTH: 3909
<212> TYPE: DNA
<213> ORGANISM: Artificial Sequence
<220> FEATURE:
<223> OTHER INFORMATION: Synthesized

<400> SEQUENCE: 3

```
gatgtcacta ggtgctcagc taacactaat tttaggcgtt tcttttcaaa atttaatgtt      60
caggcgcctg cagttgttgt actgggcggt tatctaccta ttggtgaaaa ccagggtgtc     120
aattcaactt ggtactgtgc tggccaacat ccaactgcta gtggcgttca tggtatcttt     180
gttagccata ttagaggtgg tcatggcttt gagattggca tttcgcaaga gccttttgac     240
cctagtggtt accagcttta tttacataag gctactaacg gtaacactaa tgctactgcg     300
cgactgcgca tttgccagtt tcctagcatt aaaacattgg gccccactgc taataatgat     360
gttacaacag tcgtaattg cctatttaac aaagccatcc cagctcatat gagtgaacat     420
agtgttgtcg aataacatg gataatgat cgtgtcactg tcttttctga caagatctat     480
tattttatt ttaaaaatga ttggtcccgt gttgcgacaa agtgttacaa cagtggaggt     540
tgtgccatgc aatatgttta cgaacccacc tattacatgc ttaatgttac tagtgctggt     600
gaggatggta tttcttatca accctgtaca gctaattgca ttggttatgc tgccaatgta     660
tttgctactg agcccaatgg ccacatacca gaaggtttta gttttaataa ttggtttctt     720
ttgtccaatg attccacttt ggtgcatggt aaggtggttt ccaaccaacc attgttggtc     780
aattgtcttt ggccattcc taagattat ggactaggcc aatttttctc ctttaatcaa     840
acgatcgatg gtgtttgtaa tggagctgct gtgcagcgtg caccagaggc tctgaggttt     900
aatattaatg acacctctgt cattcttgct gaaggctcaa ttgtacttca tactgcttta     960
ggaacaaatt tttcttttgt ttgcagtaat tcctcagatc ctcacttagc caccttcgcc    1020
atacctctgg gtgctatcca agtacccctat tattgttttc ttaaagtgga tacttacaac    1080
```

```
tccactgttt ataaattctt ggctgtttta cctcctaccg tcagggaaat tgtcatcacc    1140
aagtatggtg atgtttatgt caatgggttt ggctatttgc atctcggttt gttggacgct    1200
gtcacaatta atttcactgt tcatggcact gacgatgacg tttcaggttt ctggaccata    1260
gcatcgacta attttgttga tgcacttatc gaagttcaag gaactgccat tcagcgtatt    1320
ctttattgtg atgatcctgt tagccaactc aagtgttctc aggttgcttt tgaccttgac    1380
gatggtttct accctatttc ttctagaaac cttctgagtc atgaacagcc aatttctttt    1440
gttactttgc catcatttaa tgatcattct tttgttaaca ttactgtctc tgcgtccttt    1500
ggtggtcata gtggtgccaa ccttattgca tctgacacta ctatcaatgg gtttagttct    1560
ttctgtgttg acactagaca atttaccatt tcactgtttt ataacgttac aaacagttat    1620
ggttatgtgt ctaaatcaca ggacagtaat tgcccttttca ccttgcaatc tgttaatgat    1680
tacctgtctt ttagtaaatt tgtgtttcc accagccttt tggctagtgc ctgtaccata    1740
gatcttttg gttaccctga gtttggtagt ggtgttaagt ttacgtccct ttactttcaa    1800
ttcacaaagg gtgagttgat tactggcacg cctaaaccac ttgaaggtgt cacggacgtt    1860
tcttttatga ctctggatgt ttgtaccaag tatactatct atggctttaa aggtgagggt    1920
atcattaccc ttacaaattc tagcttttttg gcaggttttt attacacatc tgattctgga    1980
cagttgttag cctttaagaa tgtcactagt ggtgctgttt attctgttac gccatgttct    2040
ttttcagagc aggctgcata tgttgatgat gatatagtgg gtgttatttc tagtttgtct    2100
aactccactt ttaacagtac tagggagttg cctggttttct tctaccattc taatgatggc    2160
tctaattgta cagagcctgt gttggtgtat agtaacatag gtgtttgtaa atctggcagt    2220
attggctacg ttccatccca gcctggccaa gtcaagattg cacccacggt tactgggaat    2280
attagtattc ccaccaactt tagtatgagt attaggacag aatatttaca gctttacaac    2340
acgcctgtta ttgttgattg tgccacatat gtttgtaatg gtaactctcg ttgtaaacaa    2400
ttactcaccc agtacactgc agcatgtaag accatagagt cagcattaca actcagcgct    2460
aggcttgagt ctgttgaagt taactctatg cttactattt ctgaagagtc tctacagtta    2520
gctaccatca gttcgtttaa tggtggtgga tataatttta ctaacgtgct gggtgtttct    2580
gtgtatgatc ctgcaagtgg cagggtggta caaaaaaggt ctttttattga agacctgctt    2640
tttaataaag tggttactaa tggccttggt actgttgatg aagactataa gcgctgttct    2700
aatggtcgct ctgtggcaga tctagtctgt gcacagtatt actctggtgt catggtacta    2760
cctggtgttg ttgacgctga gaagcttcac atgtatagtc gtctctcat cggtggtatg    2820
gtgctaggag gttttacttc tgcagcagca ttgccttttta gctatgctgt tcaagctaga    2880
ctcaattatc ttgctctaca gacggatgtt ctacagcgga accagcaatt gcttgctgag    2940
tcttttaact ctgctattgg taatataact tcagcctttg agagtgttaa agagtctatt    3000
agtcaaactt ccaagggttt gaacactgtg gctcatgcgc ttactaaggt tcaagaggtt    3060
gttaactcgc agggtgcagc tttgactcaa cttaccgtac agctgcaaca caacttccaa    3120
gccatttcta gttctattga tgacattgac tctcgactgg acattctttc agccgatgtt    3180
caggttgacc gtctcatcac cggcagatta tcagcactta atgcttttgt tgctcaaacc    3240
ctcactaagt atactgaggt tcaggctagc aggaagctag cacagcaaaa ggttaatgag    3300
tgcgttaaat cccaatctca gcgttatggt ttttgtggtg gtgatggcga gcacattttc    3360
tctctggtac aggcagcacc tcagggcctg ctgttttac atacagtact tgtaccgggt    3420
```

```
gactttgtag atgttattgc catcgctggc ttatgcgtta acgatgaaat tgccttgact    3480
ctacgtgagc ctggcttagt cttgtttacg catgaacttc aaaatcatac tgcgacggaa    3540
tattttgttt catcgcgacg tatgtttgaa cctagaaaac ctaccgttag tgattttgtt    3600
caaattgaga gttgtgtggt cacctatgtc aatttgacta gagaccaact accagatgta    3660
atcccagatt acatcgatgt taacaaaaca cttgatgaga ttttagcttc tctgcccaat    3720
agaactggtc caagtcttcc tttagatgtt tttaatgcca cttatctcaa tctcactggt    3780
gaaattgcag atttagagca gcgttcagag tctctccgta atactacaga ggagctccaa    3840
agtcttatat ataatatcaa caacacacta gttgaccttg agtggctcaa ccgagttgag    3900
acatacatc                                                             3909
```